US007550293B2

(12) United States Patent
Bencherif et al.

(10) Patent No.: US 7,550,293 B2
(45) Date of Patent: Jun. 23, 2009

(54) CHIMERIC NICOTINIC RECEPTOR SUBUNITS

(75) Inventors: Merouane Bencherif, Winston-Salem, NC (US); Ronald J. Lukas, Phoenix, AZ (US)

(73) Assignees: Targacept, Inc., Winston-Salem, NC (US); Catholic Healthcare West, San Francisco, CA (US)

( * ) Notice: Subject to any disclaimer, the term of this patent is extended or adjusted under 35 U.S.C. 154(b) by 529 days.

(21) Appl. No.: 11/037,829

(22) Filed: Jan. 18, 2005

(65) Prior Publication Data
US 2005/0255551 A1 Nov. 17, 2005

Related U.S. Application Data

(63) Continuation of application No. PCT/US03/22550, filed on Jul. 18, 2003.

(60) Provisional application No. 60/397,380, filed on Jul. 19, 2002.

(51) Int. Cl.
*C12N 5/10* (2006.01)
*C12N 15/12* (2006.01)
*C12N 15/63* (2006.01)
*C12N 1/21* (2006.01)
*C07K 14/00* (2006.01)

(52) U.S. Cl. .................. 435/325; 435/69.1; 435/252.3; 435/320.1; 530/350; 536/23.5

(58) Field of Classification Search ........................ None
See application file for complete search history.

(56) References Cited

U.S. PATENT DOCUMENTS

| | | | |
|---|---|---|---|
| 4,631,211 | A | 12/1986 | Houghten |
| 4,873,191 | A | 10/1989 | Wagner |
| 5,187,166 | A | 2/1993 | Kikuchi |
| 5,583,140 | A | 12/1996 | Bencherif |
| 5,597,919 | A | 1/1997 | Dull |
| 5,641,670 | A | 6/1997 | Treco |
| 5,672,601 | A | 9/1997 | Cignarella |
| 5,852,041 | A | 12/1998 | Cosford |
| 6,638,925 | B2 | 10/2003 | Czollner |

FOREIGN PATENT DOCUMENTS

| | | |
|---|---|---|
| CA | 2045869 | 12/1991 |
| EP | 0 297 858 | 1/1989 |
| GB | 2 295 387 | 5/1996 |
| WO | WO 87/01130 | 2/1987 |
| WO | WO 93/13423 | 7/1993 |
| WO | WO 94/08992 | 4/1994 |
| WO | WO 94/12650 | 6/1994 |
| WO | WO 96/29411 | 9/1996 |
| WO | WO 96/31475 | 10/1996 |
| WO | WO 96/40682 | 12/1996 |
| WO | WO 99/21834 | 5/1999 |

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*

Skolnick et al. (2000). From genes to protein structure and function: novel applications of computational approaches in the genomic era. Trends in Biotechnology. 18:34-39.*

Wang et al. (1999). Rapid analysis of gene expression (RAGE) facilitates universal expression profiling. Nucleic Acds Research. 27(23):4609-4618.*

Kaufman et al. (1999). Transgenic analysis of a 100-kb human B-globulin cluster-containing DNA fragment propagated as a bacterial artificial chromosome. Blood. 94(9):3178-3184.*

Arneric, S., et al., "Preclinical Pharmacology of ABT-418: A Prototypical Cholinergic Channel Activator for the Potential Treatment of Alzheimer's Disease," *CNS Drug Rev.*, 1(1): 1-26 (1995).

Arneric, S., et al., "Cholinergic channel modulators as a novel therapeutic strategy for Alzheimer's disease," *Exp. Opin. Invest. Drugs*, 5(1): 79-100 (1996).

Bannon, A.W., et al., "Broad-Spectrum, Non-Opioid Analgesic Activity by Selective Modulation of Neuronal Nicotinic Acetylcholine Receptors," *Science*, 279: 77-80 (1998).

Bencherif, M., et al., "RJR-2403: A Nicotinic Agonist with CNS Selectivity I: In Vitro Characterization," *J. Pharmacol. Exper. Therapeutics*, 279(3): 1413-1421 (1996).

Bencherif, M, and R.J. Lukas, "Cytochalasin Modulation of Nicotinic Cholinergic Receptor Expression and Muscarinic Receptor Function in Human TE671/RD Cells: A Possible Functional Role of the Cytoskeleton," *Journal of Neurochemistry*, 61: 852-864 (1993).

Bennett, D., et al., "Kinetic Characterization of the Interaction of Biotinylated Human Interleukin 5 with an Fc Chimera of its Receptor α Subunit and Development of an ELISA Screening Assay using Real-Time Interaction Biosensor Analysis," *J. Mol. Recog.*, 8: 52-58 (1995).

Boulter, J., et al., "Isolation of a cDNA clone coding for a possible neural nicotinic acetylcholine receptor α-Subunit," *Nature*, 319(6052): 368-374 (1986).

Brioni, J.D., et al., "The Pharmacology of (−)-Nicotine and Novel Cholinergic Channel Modulators," *Adv. Pharmacol.*, 37: 153-215 (1997).

Brutlag, D.L., et al., "Improved sensitivity of biological sequence database searches," *Comp. Ap. Biosc.* 6(3): 237-245 (1990).

(Continued)

*Primary Examiner*—Christine J Saoud
*Assistant Examiner*—Jon M Lockard
(74) *Attorney, Agent, or Firm*—Womble Carlyle Sandridge & Rice, PLLC

(57) ABSTRACT

A chimeric nAChR receptor subunit polypeptide having a substitution of at least about 15% of the native amino acid sequence of the subunit in the area of the C-terminal cytoplasmic domain is provided, as well as polynucleotides encoding the polypeptide. Vectors, host cells, and related methods for evaluating compounds are also provided.

6 Claims, 11 Drawing Sheets

OTHER PUBLICATIONS

Buckle, V.J., et al., "Chromosomal Localization of GABA$_A$ Receptor Subunit Genes: Relationship to Human Genetic Disease," *Neuron.*, 3(5): 647-654 (1989).

Campbell, K.H.S., et al., "Sheep cloned by nuclear transfer from a cultured cell line," *Nature*, 380: 64-66 (1996).

Carver, A.S., et al., "Transgenic Livestock as Bioreactors: Stable Expression of Human Alpha-1-Antitrypsin by a Flock of Sheep," *Biotechnology*, 11: 1263-1270 (1993).

Campos-Caro, A., et al., "A single residue in the M2-M3 loop is a major determinant of coupling between binding and gating in neuronal nicotinic receptors," *Pro. Natl. Acad. Sci.*, 93(12): 6118-6123 (1996).

Chiari, A., et al., "Sex Differences in Cholinergic Analgesia I: A Supplemental Nicotinic Mechanism in Normal Females," *Anesthesiology*, 91(5): 1447-1454 (1999).

Cleland, J.L., et al., "The Development of Stable Protein Formulations: A Close Look at Protein Aggregation, Deamidation, and Oxidation," *Crit. Rev. Therapeutic Drug Carrier Systems*, 10(4): 307-377 (1993).

Clementi, F., et al., "Pharmacological Characterization of Cholinergic Receptors in a Human Neuroblastoma Cell Line," *J. Neurochem.*, 47(1): 291-297 (1986).

Cleveland, D.W., et al., "Number and Evolutionary Conservation of a α- and β- Tubulin and Cytoplasmic β- and γ- Actin Genes Using Specific Cloned cDNA Probes," *Cell*, 20: 95-105 (1980).

Colledge M. and S.C. Froehner, "Tyrosine Phosphorylation of Nicotinic Acetylcholine Receptor Mediates Grb2 Binding," *J. Neurosci.*, 17(13): 5038-5045 (1997).

Cooper, S.T., and N.S. Millar, "Host Cell-Specific Folding of the Neuronal Nicotinic Receptor α8 Subunit," *J. Neurochem.*, 70: 2585-2593 (1998).

Cooper, S.T., et al., "Up-regulation of Cell-surface α4β2 Neuronal Nicotinic Receptors by Lower Temperature and Express of Chimeric Subunits," *The Journal of Biological Chemistry*, 274(38): 27145-27152 (1999).

Corringer P-J, et al., "Nicotinic Receptors at the Amino Acid Level," *Annu. Rev. Pharmacol. Toxicol.*, 40: 431-458 (2000).

Cunningham, B.C., and J.A. Wells, "High-Resolution Epitope Mapping of hGH-Receptor Interactions by Alanine-Scanning Mutagenesis," *Science*, 244: 1081-1085 (1989).

Dajas-Bailador, F.A., et al., "Nicotine activates the extracellular signal-regulated kinase ½ via the α7 nicotinic acetylcholine receptor and protein kinase A, in SH-SY5Y cells and hippocampal neurons," *J. Neurochem.*, 80: 520-530 (2002).

Damaj, M.I., et al., "Antinociceptive and Pharmacological Effects of Metanicotine, a Selective Nicotinic Agonist," *J. Pharmacol. Exp. Ther.*, 291(1): 390-398 (1999).

Dascal, D., "The Use of *Xenopus* Oocytes for the Study of Ion Channels," *Crit. Rev. Biochem.*, 22(4): 317-387(1987).

Decina, P., et al. "Cigarette Smoking and Neuroleptic-Induced Parkinsonism," *Biol. Psychiatry*, 28: 502-508 (1990).

Deneris, E.S., et al., "Pharmacological and functional diversity of neuronal nicotinic acetylcholine receptors," *TIPS*, 121: 34-40 (1991).

Devillers-Thiery, A., et al., "Functional Architecture of the Nicotinic Acetylcholine Receptor: A Prototype of Ligand-gated Ion Channels," *J. Membrane Biol.*, 136: 97-112 (1993).

De Vos, A., et al., "Human Growth Hormone and Extracellular Domain of Its Receptor: Crystal Structure of the Complex," *Science*, 255: 306-312 (1992).

Eaton, J.B., et al., "Characterization of Human α4β2—Nicotinic Acetylcholine Receptors Stably and Heterologously Expressed in Native Nicotinic Receptor-Null SH-EP1 Human Epithelial Cells," *Mol. Pharmacol.*, 64(6): 1283-1294 (2003).

Eisele, J-L., et al., "Chimaeric nicotinic-serotonergic receptor combines distinct ligand binding and channel specificities," *Nature*, 366: 479-483 (1993).

Fenster, C.P., et al., "Regulation of α4β2 Nicotinic Receptor Desensitations by Calcium and Protein Kinase C," *C. Mol. Pharmacol.*, 55: 432-443 (1999).

Fenster, C.P., et al., "Upregulation of Surface α4β2 Nicotinic Receptors Is Initiated by Receptor Desensitization after Chronic Exposure to Nicotine," *The Journal of Neuroscience*, 19(12): 4804-4814 (1999).

Gentz, R., et al., "Bioassay for trans-activation using purified human immunodeficiency virus *tat*-encoded protein: Trans-activation requires mRNA synthesis," *Pro. Nat. Acad. Sci. USA*, 86: 821-824 (1989).

Gordon, J.W., "Transgenic Animals," *Intl. Rev. Cytol.*, 115: 171-229 (1989).

Gu, H., et al., "Deletion of a DNA Polymerase β Gene Segment in T Cells Using Cell Type-Specific Gene Targeting," *Science*, 265(5168): 103-106 (1994).

Guo, X., and L. Wecker, "Identification of three cAMP-dependent protein kinase (PKA) phosphorylation sites within the major intracellular domain of neuronal nicotinic receptor α4 subunits," *J. Neurochem.*, 82: 439-447 (2002).

Hall, G.H., and D.M. Turner, "Effects of Nicotine on the Release of $^3$H-Noradrenaline from the Hypothalamus," *Biochemical Pharmacology*, 21: 1829-1838 (1972).

Hamon, M., "Neuropharmacology of anxiety: perspectives and prospects," *TiPS*, 15: 36-39 (1994).

Hampson, D.R., et al., "Solubilization of Kainic Acid Binding Sites from Rat Brain," *J. Neurochem.*, 1209-1215 (1987).

Hanna, M.C., et al., "Evidence for Expression of Heteromeric Serotonin 5-HT(3) Receptors in Rodents," *J. Neurochem.*, 75(1): 240-247 (2000).

Harkness, P.C., and N.S. Millar, "Changes in Conformation and Subcellular Distribution of α4β2 Nicotinic Acetylcholine Receptors Revealed by Chronic Nicotine Treatment and Expression of Subunit Chimeras," *The Journal of Neuroscience*, 22(23): 10172-10181 (2002).

Harsing, L.G., et al., Dopamine Efflux from Striatum After Chronic Nicotine: Evidence for Autoreceptor Desensitization, *J. Neurochem.*, 59(1): 48-54 (1992).

Hery, F., et al., "Control of the Release of Newly Synthetized $^3$H-5-Hydroxytryptamine by Nicotinic and Muscarinic Receptors in Rat Hypothalamic Slices," *Naunyn-Schmiedeberg's Arch. Pharmacol.*, 296: 91-97 (1977).

Holladay, M.W., et al., "Neuronal Nicotinic Acetylcholine Receptors as Targets for Drug Discovery," *J. Med. Chem.*, 40(26): 4169-4194 (1997).

Houghten, R.A., "General method for the rapid solid-phase synthesis of large umbers of peptides: Specificity of antigen-antibody interaction at the level of individual amino acids," *Proc. Natl. Acad. Sci USA*, 82: 5131-5135 (1985).

Huganir, R.L., and P. Greengard, "Regulation of Neurotransmitter Receptor Desensitization by Protein Phosphorylation," *Neuron*, 5: 555-567 (1990).

Johanson, K., et al., "Binding Interactions of Human Interleukin 5 with Its Receptor α Subunit," *J. Biol. Chem.*, 270(16): 9459-9471 (1995).

Karlin, A., "Emerging Structure of the Nicotinic Acetylcholine Receptors," *Nat. Rev. Neurosci.* 3: 102-114 (2002).

Kelly, S.P., et al., "A cytoplasmic region determine single-channel conductance in 5-HT(3) receptors," *Nature*, 321-324 (2003).

Koller, B.H., and O. Smithies, "Inactivating the β2-microglobulin locus in mouse embryonic stem cells by homologous recombination," *Proc. Natl. Acad. Sci. USA*, 86: 8932-8935 (1989).

Ku, Y.P., et al., "Characterization of Human Wild-Type α4-Chimeric β 2-Nicotinic Acetylcholine Receptors Stably Expressed in SH-EPI Cells," Program No. 537.13, *Abstract Viewer/Itinerary Planner, Society for Neuroscience* (2002).

Lasko, M., et al., "Targeted oncogene activation by site-specific recombination in transgenic mice," *Proc. Natl. Acad. Sci. USA*, 89: 6232-6236 (1992).

Lavand'homme, P., and J.C. Eisenach, "Sex Differences in Cholinergic Analgesia II; Differing Mechanisms in Two Models of Allodynia," *Anesthesiology*, 91(5): 1455-1461 (1999).

Lavitrano, M., et al., "Sperm Cells as Vectors for Introducing Foreign DNA into Eggs: Genetic Transformation of Mice," *Cell*, 57: 717-723 (1989).

Lippiello, P.M., et al., "RJR-2403: A Nicotinic Agonist with CNS Selectivity II. In Vivo Characterization," *J. P. E. T.*, 279(3): 1422-1429 (1996).

Lo, C.W., "Transformation by Iontophoretic Microinjection of DNA: Multiple Integrations Without Tandem Insertions," *Mol. Cell. Biol.*, 3(10): 1803-1814 (1983).

Lukas, R.J., "Neuronal Nicotinic Acetylcholine Receptors," *The Nicotinic Acetylcholine Receptors: Current Views and Future Trends*, F.J. Barrantes, Editor., Springer Verlag, Berlin/Heidelberg and Landes Publishing: Georgetown, TX. p. 145-173 (1998).

Lukas, R.J., et al., "Some Methods of Studies of Nicotinic Acetylcholine Receptor Pharmacology," Ch. 1, in *Methods & New Frontiers in Neuroscience*, CRC Press LLC, p. 3-27 (2002).

Maricq, A.V., et al., "Primary Structure and Functional Expression of the 5HT(3) Receptor, a Serotonin-Gated Ion Channel," *Science*, 254(5030): 432-437 (1991).

Marks, M.J., and A.C. Collins, "Characterization of Nicotine Binding in Mouse Brain and Comparison with the Binding of α-Bungarotoxin and Quinuclidinyl Benzilate," *Molec. Pharmacol.*, 22: 554-564 (1982).

Morgado-Valle, C., et al., "A motif present in the main cytoplasmic loop of nicotinic acetylcholine receptors and catalases," *Pro. R. Soc. Lond. B. Biol. Sci.*, 268: 967-972 (2001).

Noda, M., et al., "Primary structure of α-subunit precursor of Torpedo californica acetylcholine receptor deduced from cDNA sequence," *Nature*, 299: 793-797 (1982).

Onaivi, E.D., et al., "Chronic Nicotine Reverses Age-Associated Increases in Tail-Flick Latency and Anxiety in Rats," *Life Sciences*, 54(3): 193-202 (1993).

Ostade, X.V., et al., "Human TNF mutants with selective activity on the p55 receptor," *Nature*, 361: 266-269 (1993).

Paterson, T. et al., "Approaches to maximizing stable expression of $\alpha_1$antitrypsin in transformed CHO Cells," *Appl. Microbiol. Biotechnol.*, 40: 691-698 (1994).

Patrick, J., et al., "Acetylcholine Receptor Metabolism in a Nonfusing Muscle Cell Line," *J. Biol. Chem.*, 252(6): 2143-2153 (1977).

Perez-Reyes, E., et al., "Induction of calcium currents by the express of the $\alpha_1$-subunit of the dihydropyridine receptor from skeletal muscle," *Nature*, 340: 233-236 (1989).

Pinckard, R.N., et al., "Factors influencing in the immune response," *Clin. Exp. Immunol.*, 2: 331-341 (1967).

Pierce, K.D., et al., "A Nonsense Mutation in the α1 Subunit of the Inhibitory Glycine Receptor Associated with Bovine Myoclonus," *Mol. Cell. Neurosci.*, 17(2): 354-363 (2001).

Pomerleau, O.F., et al., "The Effects of Cigarette Smoking on Pain and Anxiety," *Addictive Behaviors*, 9: 265-271 (1984).

Pullan, R.D., et al. "Transdermal Nicotine for Active Ulcerative Colitis," *New England J. Med.*, 330(12): 811-815 (1994).

Rapier, C., et al., "Stereoselective Nicotine-Induced Release of Dopamine from Striatal Synaptosomes: Concentration Dependence and Repetitive Stimulation," *J. Neurochem.*, 50: 1123-1130 (1988).

Robins, D.C., et al., "Antibodies to Covalent Aggregates of Insulin in Blood of Insulin-Using Diabetic Patients," *Diabetes*, 36: 838-841 (1987).

Ross, R.A., et al., "Coordinate Morphological and Biochemical Interconversion of Human Neuroblastoma Cells," *JNCI*, 71(4): 741-747 (1983).

Rowell, P. P., and D. L. Winkler, "Nicotinic Stimulation of [$^3$H] Acetylcholine Release from Mouse Cerebral Cortical Synaptosomes," *J. Neurochem.*, 43(6): 1593-1598 (1984).

Sanberg, et al., "Nicotine Potentiation of Haloperidol-Induced Catalepsy: Striatal Mechanisms," *Pharmacol. Biochem. & Behavior*, 46: 303-307 (1993).

Sandor, et al. "Effect of nicotine on dopaminergic-cholinergic interaction in the striatum," *Brain Res.*, 567: 313-316 (1991).

Shaw, S., et al., "Janus Kinase 2, an Early Target of α7 Nicotinic Acetylcholine Receptor-mediated Neuroprotection against Aβ-(1-42) Amyloid," *J. Biol. Chem.*, 277(47): 44920-44924 (2002).

Sanes, J.R., et al., "Use of a recombinant retrovirus to study post-implantation cell lineage in mouse embryos," *The EMBO Journal*, 4(12): 3133-3142 (1986).

Shoop, R.D., et al., "Cytoskeletal Links of Neuronal Acetylcholine Receptors Containing α7 Subunits," *J. Neurosci.*, 20(11): 4021-4029 (2000).

Sgard, F., et al., "A Novel Human Nicotinic Receptor Subunit, α10, That Confers Functionality to the α9-Subunit," *Molecular Pharmacology*, 61(1): 150-159 (2002).

Sine, S.M., "The Nicotinic Receptor Ligand Binding Domain," *J. Neurobiol.*, 53: 431-446 (2002).

Sjak-Shie, N.N., and E.M. Meyer, "Effects of chronic nicotine and pilocarpine administration on neocortocal neuronal density and [$^3$H]GABA uptake in nucleus basalis lesioned rats," *Brain Res.*, 624: 295-298 (1993).

Smith, L.J., et al., "Human Interleukin 4 The Solution Structure of a Four-helix Bundle Protein," *J. Mol. Biol.*, 224: 899-904 (1992).

Smith, D.B., and K.S. Johnson, "Single-step purification of polypeptides expressed in *Escherichia coli* as fusions with glutathione S-transferase," *Gene*, 67: 31-40 (1988).

Thompson, S., et al., "Germ Line Transmission and Expression of a Corrected HPRT Gene Produced by Gene Targeting in Embryonic Stem Cells," *Cell*, 56: 313-321 (1989).

Tobimatsu, T., et al., "Effects of substitution of putative transmembrane segments on nicotinic acetylcholine receptor function," *FEBS Lett.*, 222(1): 56-62.

Toth, E., et al., "Effect of Nicotine of Extracellular Levels of Neurotransmitters Assessed by Microdialysis in Various Brain Regions: Role of Glutamic Acid," *Neurochem. Res.*, 17(3): 265-270 (1992).

Tripathi, et al., "Nicotine-Induced Antinociception of Rats and Mice: Correlation with Nicotine Brain Levels," *J. Pharmacol. Exp. Ther.*, 221(1): 91-96 (1982).

Ulmer, J.B., et al., "Heterologous Protection Against Influenza by Injection of DNA Encoding a Viral Protein," *Science*, 259: 1745-1749 (1993).

Valor, L.M., et al., "Role of the Large Cytoplasmic Loop of the α7 Neuronal Nicotinic Acetylcholine Receptor Subunit in Receptor Expression and Function," *Biochemistry*, 41(25): 7931-7938 (2002).

Van der Putten, H., et al., "Efficient insertion of genes into the mouse germ line via retroviral vectors," *Proc. Natl. Acad. Sci USA*, 82: 6148-6152 (1985).

Verrall, S. and Z.W. Hall, "The N-Terminal Domains of Acetylcholine Receptor Subunits Contain Recognition Signals for the Initial Steps of Receptor Assembly," Cell, 68: 23-31 (1992).

Vizi, E.S., "Acetylcholine release from guinea-pig ileum by parasympathetic ganglion stimulants and gastrin-like polypeptides," *Br. J. Pharmac.*, 47: 765-777 (1973).

Wagner, B., et al., "Does Smoking Reduce the Risk of Neuroleptic Parkinsonoids?," *Pharmacopsychiat.*,. 21: 302-303 (1988).

Wigler, M., et al., "DNA-mediated transfer of the adenine phosphoribosyltransferase locus into mammalian cells," *Proc. Natl. Acad. Sci. USA*, 76(3): 1373-1376 (1979).

Williams, B.M., et al., "The long internal loop of the α3 subunit targets nAChRs to subdomains within individual synapses on neurons in vivo," *Nat. Neurosci.*, 1(7): 557-562 (1998).

Williams, M., et al., "Neuronal Nicotinic Acetylcholine Receptors," *Drug News Perspec.*, 7(4): 205-223 (1994).

Wilmut, I., et al., "Viable offspring derived from fetal and adult mammalian cells," *Nature*, 385: 810-813 (1997).

Wilson, I.A., et al., "The structure of an antigenic determinant in a protein," *Cell*, 37: 767-778 (1984).

Wright, G., et al., "High Level Expression of Active Human Alpha-1-Antitrypsin in the Milk of Transgenic Sheep," *Biotechnology*, 9: 830-834 (1991).

Yu, X-M., and Z.W. Hall, "The role of the cytoplasmic domains of individual subunits of the acetylcholine receptor in 43 kDa Protein-Induced Clustering in COS Cells," *J. Neurosci.*, 14(2): 785-795 (1994).

Yu, X-M., and Z.W. Hall, "A Sequence in the Main Cytoplasmic Loop of the α Subunit is Required for Assembly of Mouse Muscle Nicotinic Acetylcholine Receptor," *Neuron*, 13: 247-255 (1994).

Zijlstra, M. et al., "Germ-line transmission of a disrupted $\beta_2$-microglobulin gene produced by homologous recombination in embryonic stem cells," *Nature*, 342: 435-438 (1989).

\* cited by examiner

FIG. 1A (hAlpha4, SEQ ID NO:1; hBeta2, SEQ ID NO:2; hBeta4, SEQ ID NO:3;
h5HT3, SEQ ID NO:4; and m5HT3, SEQ ID NO:5)

```
hAlpha4   MELGGPGAPR LLPPLLLLLG TGLLRASSHV ETR.AHAEE. .......RLL KKLFSG..YN  49
hBeta2    M.......AR RCGPVALLLG FGLLRLCS.. GVWGADTEE. .......RLV EHLLDPSRYN  43
hBeta4    M.......RR ...APSLVLF F.LVALCGRG NCRVANAEE. .......KLM DDLLNKTRYN  41
h5HT3     MLL....... WVQQALLALL LPTLLAQGEA RR.....SRN TTRPALLRLS DYLL..TNYR  46
m5HT3     MRL....... CIPQVLLALF LSMLTAPGEG SRRRATQARD TTQPALLRLS DHLL..ANYK  51 hAlpha4   KWSRPVANIS DVVLVRFGLS IAQLIDVDEK NQMMTTNVWV KQEWHDYKLR WDPADYENVT  109
hBeta2    KLIRPATNGS ELVTVQLMVS LAQLISVHER EQIMTTNVWL TQEWEDYRLT WKPEEFDNMK  103
hBeta4    NLIRPATSSS QLISIKLQLS LAQLISVNER EQIMTTNVWL KQEWTDYRLT WNSSRYEGVN  101
h5HT3     KGVRPVRDWR KPTTVSIDVI VYAILNVDEK NQVLTTYIWY RQYWTDEFLQ WNPEDFDNIT  106
m5HT3     KGVRPVRDWR KPTTVSIDVI MYAILNVDEK NQVLTTYIWY RQYWTDEFLQ WTPEDFDNVT  111 hAlpha4   SIRIPSELIW RPDIVLYNNA DGDFAVTHLT KAHLFHDGRV QWTPPAIYKS SCSIDVTFFP  169
hBeta2    KVRLPSKHIW LPDVVLYNNA DGMYEVSFYS NAVVSYDGSI FWLPPAIYKS ACKIEVKHFP  163
hBeta4    ILRIPAKRIW LPDIVLYNNA DGTYEVSVYT NLIVRSNGSV LWLPPAIYKS ACKIEVKYFP  161
h5HT3     KLSIPTDSIW VPDILINEFV DVG.KSPNIP YVYIRHQGEV QNYKPLQVVT ACSLDIYNFP  166
m5HT3     KLSIPTDSIW VPDILINEFV DVG.KSPNIP YVYVHHRGEV QNYKPLQLVT ACSLDIYNFP  171 hAlpha4   FDQQNCTMKF GSWTYDKAKI DLVN....MH SRVDQLDFWE SGEWVIVDAV GTYNTRKYEC  225
hBeta2    FDQQNCTMKL RSWTYDRTEI DLVL....KS EVASLDDFTP SGEWDIVALP GR...RNENP  216
hBeta4    FDQQNCTLKF RSWTYDHTEI DMVL....MT PTASMDDFTP SGEWDIVALP GR...RTVNP  214
h5HT3     FDVQNCSLTF TSWLHTIQDI NISLWRLPEK VKSDRSVFMN QGEWELLGVL PYFREFSMES  225
m5HT3     FDVQNCSLTF TSWLHTIQDI NITLWRSPEE VRSDKSIFIN QGEWELLEVF PQFKEFSIDI  230 hAlpha4   CAEIYPDITY AFVIRRLPLF YTINLIIPCL LISCLTVLVF YLPSECGEKI TLCISVLLSL  285
hBeta2    DDSTYVDITY DFIIRRKPLF YTINLIIPCV LITSLAILAF YLPSDCGEKM TLCISVLLAL  276
hBeta4    QDPSYVDVTY DFIIKRKPLF YTINLIIPCV LTTLLAILVF YLPSDCGEKM TLCISVLLAL  274
h5HT3     .SNYYAEMKF YVVIRRRPLF YVVSLLLPSI FLMVMDIVGF YLPPNSGERV SFKITLLLGY  284
m5HT3     .SNSYAEMKF YVIIRRRPLF YAVSLLLPSI FLMVVDIVGF CLPPDSGERV SFKITLLLGY  289
                                                   M3
hAlpha4   TVFLLLITEI IPSTSLV PL  IGEYLLFTMI FVTLSIVITV FVLN HHRSP RTHTMPTWVR  345
hBeta2    TVFLLLISKI VPPTSLD PL  VGKYLMFTMV LVTFSIVTSV CVLN HHRSP TTHTMAPWVK  336
hBeta4    TFFLLLISKI VPPTSLD PL  IGKYLMFTMV LVTFSIVTSV CVLN HHRSP STHTMAPWVK  334
h5HT3     SVFLIIVSDT LPATAIGTPL IGVYFVVCMA LLVISLAETI FIVRLVHKQD LQQPVPAWLR  344
m5HT3     SVFLIIVSDT LPATAIGTPL IGVYFVVCMA LLVISLAETI FIVRLVHKQD LQRPVPDWLR  349
```

FIG. 1B

```
hAlpha4   RVFLDIVPRL LLMKRPSVVK DNCRRLIESM HKMASAPRFW PEPEGEPPAT SGTQSLHPPS 405
hBeta2    VVFLEKLPAL LFMQQPRHHC ARQR.L.... ....RLRRRQ REREGAGALF FREAPGADSC 387
hBeta4    RCFLHKLPTF LFMKRPGPDS SPARAF.... ....PPSKSC VTKPEATATS TSPSNFYGNS 386
h5HT3     HLVLERIAWL LCLR...... .......... .......... .......... .......... 358
m5HT3     HLVLDRIAWI LCLG...... .......... .......... .......... .......... 363 hAlpha4   PSFCVPLDVP AEPGPSCKSP SDQLPPQQPL EAEKASPHPS PGPCRPSHGT QAPGLAKARS 465
hBeta2    TCFVNRASVQ GLAGAFGAEP A......... .......... .......... .......... 408
hBeta4    MYFVNPASAA SKSPA.GSTP V......... .......... .......... .......... 406
h5HT3     .......... .......... .......... ..EQSTSQRP PATSQATKTD DCSAMGNHCS 386
m5HT3     .......... .......... .......... ..EQPMAHRP PATFQANKTD DCSAMGNTCS 391 hAlpha4   LSVQHMSSPG EAVEGGVRCR SRSIQYCVPR DDAAPEADGQ AAGALASRNT HSAELPPPDQ 525
hBeta2    .......... .PVAGP..GR S......... .......... .......... .......... 416
hBeta4    .......... .AIPRDFWLR S......... .......... .......... .......... 416
h5HT3     ....HMGGPQ DFEKS..... ........PR DRCSP..... .......... ....PPPPRE 410
m5HT3     ....HVGGPQ DLEKT..... ........PR GRGSP..... .......... ....LPPPRE 415 hAlpha4   PSPCKCTCKK EPSSVSPSAT VKTRSTKAPP PHLPLSPALT RAVEGVQYIA DHLKAEDTDF 585
hBeta2    GEPCGC.... .......... .......... ......GLR  EAVDGVRFIA DHMRSEDDDQ 445
hBeta4    SGRFRQ.... .......... .......... ......DVQ  EALEGVSFIA QHMKNDDEDQ 445
h5HT3     AS........ .......... .......... ..LAVC.GLL QELSSIR... QFLEKRDEIR 436
m5HT3     AS........ .......... .......... ..LAVR.GLL QELSSIR... HFLEKRDEMR 441
                                                   M4
hAlpha4   SVKEDWKYVA MVIDRIFLWM FIIVCLLGTV GLFLPPWL.. .......... ......AGMI 627
hBeta2    SVSVDWKYVA MVIDRLFLWI FVFVCVFGTI GMFLQPLFQN YTTTTFLHSD HSAPSSK    502
hBeta4    SVVEDWKYVA MVVDRLFLWV FMFVCVLGTV GLFLPPLFQT HAASE..... G.PYAAQRD  498
h5HT3     EVARDWLRVG SVLDKLLFHI YLLAVLAYSI TLVMLWSIWQ YA                    478
m5HT3     EVARDWLRVG YVLDRLLFRI YLLAVLAYSI TLVTLWSIWH YS                    484
```

FIG. 2 cDNA Sequence of human nAChRα4-mouse 5HT3-Flag chimera (SEQ ID NO:6)

```
CCATGGAGCTAGGGGGCCCCGGAGCGCCGCGGCTGCTGCCGCCGCTGCTGCTGCTTCTGGGGACCGGCCTCCTGCGCG
CCAGCAGCCATGTGGAGACCCGGGCCCACGCCGAGGAGCGGCTCCTGAAGAAACTCTTCTCCGGTTACAACAAGTGGT
CCCGACCCGTGGCCAACATCTCGGACGTGGTCCTCGTCCGCTTCGGCCTGTCCATCGCTCAGCTCATTGACGTGGATG
AGAAGAACCAGATGATGACCACGAACGTATGGGTGAAGCAGGAGTGGCACGACTACAAGCTGCGCTGGGACCCAGCTG
ACTATGAGAATGTCACCTCCATCCGCATCCCCTCCGAGCTCATCTGGCGGCCGGACATCGTCCTCTACAACAATGCTG
ACGGGGACTTCGCGGTCACCCACCTGACCAAGGCCCACCTGTTCCATGACGGGCGGGTGCAGTGGACTCCCCCGGCCA
TTTACAAGAGCTCCTGCAGCATCGACGTCACCTTCTTCCCCTTCGACCAGCAGAACTGCACCATGAAATTCGGCTCCT
GGACCTACGACAAGGCCAAGATCGACCTGGTGAACATGCACAGCCGCGTGGACCAGCTGGACTTCTGGGAGAGTGGCG
AGTGGGTCATCGTGGACGCCGTGGGCACCTACAACACCAGGAAGTACGAGTGCTGCGCCGAGATCTACCCGGACATCA
CCTATGCCTTCGTCATCCGGCGGCTGCCGCTCTTCTACACCATCAACCTCATCATCCCCTGCCTGCTCATCTCCTGCC
TCACCGTGCTGGTCTTCTACCTGCCCTCCGAGTGCGGCGAGAAGATCACGCTGTGCATCTCCGTGCTGCTGTCGCTCA
CCGTCTTCCTGCTGCTCATCACCGAGATCATCCCGTCCACCTCACTGGTCATCCCCCTCATTGGTGTCTACTTTGTGG
TGTGCATGGCTCTGCTAGTGATAAGCCTCGCTGAGACCATCTTCATTGTGCGGCTGGTGCATAAGCAGGACCTACAGC
GGCCAGTACCTGACTGGCTGAGGCACCTGGTCCTAGACAGAATAGCCTGGATACTCTGCCTAGGGGAGCAGCCTATGG
CCCATAGACCCCCAGCCACCTTCCAAGCCAACAAGACTGATGACTGCTCAGGTTCTGATCTTCTTCCAGCCATGGAA
ACCACTGCAGCCATGTTGGAGGACCTCAGGACTTGGAGAAGACCCCAAGGGGCAGAGGTAGCCCTCTTCCACCACCAA
GGGAGGCCTCACTGGCTGTGCGTGGTCTCTTGCAAGAGCTATCCTCCATCCGCCACTTCCTGGAGAAGCGGGATGAGA
TGCGGGAGGTGGCAAGGGACTGGCTGCGGGTGGGATACGTGCTGGACAGGCTGCTGTTCCGCATCTACCTGCTGGCTG
TGCTCGCTTACAGCATCACCCTGGTCACTCTCTGGTCCATTTGGCATTATTCTGTGGAGGATTACAAGGACGATGATG
ACAAGTGAGTCTCAGGCAGGGCGCATGCTCAGAGCAGCTCTCCTGCCTGCCTCTACAGTGACTGTGTCTCTTGCCTGC
TGGTTGTGATCCCTGGATACTCGGGCGTTTGTGTCACCCTACAACCCCTGTCCCCGCTGTGACTCATTTGGGTTGTGC
TGGCCTTCCCTGGGTCTCTTTCTCCCAAGCCTTGGGTGTTACGTACAGACTTTCGACTGAGAGCTGGATGGCTGTGCC
TGATACCCACCCATCCCCATGGCACCACTTGGCCTCCTGGCCTCCAGACAGATAGCCCTATTCCATCCCCTAATGGTG
AGCCAACCTGCACAGACACATAGGGGCACGGAGCCCTCAGGATGCAAGGGGTCCCTCATCAGTCCAGGAGTTCTTGGT
CACGCCTTGGAGGAAGATGGCAATGGGTTCTCTCCTAGAAGGGGATATTGCTTATGGAACATACCCGACTCCGCTGGC
AGGGACAGTCAGGAAGATGCTGCTGTCACCCTTTGTCCAGCCTCTCCAGTGAGTATTCAGGAAACTCAGTTGGCCTTA
CCTGGGCCATCTCAAAGGTTCCAGGATAACCCCCACTCTCCTAGCCTCCACCCTCCTAAACACTCTCCTCCCCCAGCC
CTGTTGGCACAGCATAGCTCTAGA
```

FIG. 3

**Protein Sequence of human nAChRα4-mouse 5HT3-Flag chimera
(SEQ ID NO:7)**

MELGGPGAPRLLPPLLLLLGTGLLRASSHVETRAHAEERLLKKLFSGYNKWSRPVANISDVVLVRFGLSIAQLIDVDE
KNQMMTTNVWVKQEWHDYKLRWDPADYENVTSIRIPSELIWRPDIVLYNNADGDFAVTHLTKAHLFHDGRVQWTPPAI
YKSSCSIDVTFFPFDQQNCTMKFGSWTYDKAKIDLVNMHSRVDQLDFWESGEWVIVDAVGTYNTRKYECCAEIYPDIT
YAFVIRRLPLFYTINLIIPCLLISCLTVLVFYLPSECGEKITLCISVLLSLTVFLLLITEIIPSTSLVIPLIGVYFVV
CMALLVISLAETIFIVRLVHKQDLQRPVPDWLRHLVLDRIAWILCLGEQPMAHRPPATFQANKTDDCSGSDLLPAMGN
HCSHVGGPQDLEKTPRGRGSPLPPPREASLAVRGLLQELSSIRHFLEKRDEMREVARDWLRVGYVLDRLLFRIYLLAV
LAYSITLVTLWSIWHYSLEDYKDDDDK

FIG. 4

**cDNA Sequence of human nAChRβ2-mouse 5HT3 chimera
(SEQ ID NO:8)**

CTGCCCGCGGCATGGCCCGGCGCTGCGGCCCCGTGGCGCTGCTCCTTGGCTTCGGCCTCCTCCGGCTGTGCTCAGGGG
TGTGGGGTGCGGATACAGAGGAGCGGCTGGTGGAGCATCTCCTGGATCCTTCCCGCTACAACAAGCTTATCCGCCCAG
CCACCAATGGCTCTGAGCTGGTGACAGTACAGCTTATGGTGTCACTGGCCCAGCTCATCAGTGTGCATGAGCGGGAGC
AGATCATGACCACCAATGTCTGGCTGACCCAGGAGTGGGAAGATTATCGCCTCACCTGGAAGCCTGAAGAGTTTGACA
ACATGAAGAAAGTTCGGCTCCCTTCCAAACACATCTGGCTCCCAGATGTGGTCCTGTACAACAATGCTGACGGCATGT
ACGAGGTGTCCTTCTATTCCAATGCCGTGGTCTCCTATGATGGCAGCATCTTCTGGCTGCCGCCTGCCATCTACAAGA
GCGCATGCAAGATTGAAGTAAAGCACTTCCCATTTGACCAGCAGAACTGCACCATGAAGCTCCGTTCGTGGACCTACG
ACCGCACAGAGATCGACTTGGTGCTGAAGAGTGAGGTGGCCAGCCTAGACGACTTCACACCTAGTGGTGAGTGGGACA
TCGTGGCGCTGCCGGGCCGGCGCAACGAGAACCCCGACGACTCTACGTACGTGGACATCACGTATGACTTCATCATTC
GCCGCAAGCCGCTCTTCTACACCATCAACCTCATCATCCCCTGTGTGCTCATCACCTCGCTAGCCATCCTTGCCTTCT
ACCTGCCATCCGACTGTGGCGAGAAGATGACGTTGTGCATCTCAGTGCTGCTGGCGCTCACGGTCTTCCTGCTGCTCA
TCTCCAAGATCGTGCCTCCCACCTCCCTCGACGTGCCGCTCGTCGGCAAGTACCTCATGTTCACCATGGTGCTTGTCA
CCTTCTCCATCGTCACCAGCGTGTGCGTGCTCAACGTGCACCACCGCTCGCCCACCACGCACACCATGGCGCCCTGGG
TGAGGCACCTGGTCCTAGACAGAATAGCCTGGATACTCTGCCTAGGGGAGCAGCCTATGGCCCATAGACCCCCAGCCA
CCTTCCAAGCCAACAAGACTGATGACTGCTCAGGTTCTGATCTTCTTCCAGCCATGGGAAACCACTGCAGCCATGTTG
GAGGACCTCAGGACTTGGAGAAGACCCCAAGGGGCAGAGGTAGCCCTCTTCCACCACCAAGGGAGGCCTCACTGGCTG
TGCGTGGTCTCTTGCAAGAGCTATCCTCCATCCGCCACTTCCTGGAGAAGCGGGATGAGATGCGGGAGGTGGCAGAGG
ACTGGAAGTACGTCGCCATGGTGATCGACCGCCTCTTCCTCTGGATCTTTGTCTTTGTCTGTGTCTTTGGCACCATCG
GCATGTTCCTGCAGCCTCTCTTCCAGAACTACACCACCACCACCTTCCTCCACTCAGACCACTCAGCCCCAGCTCCA
AGTGAGGCCCTTCC

FIG. 5

**Protein Sequence of human nAChRβ2-mouse 5HT3 chimera
(SEQ ID NO:9)**

MARRCGPVALLLGFGLLRLCSGVWGADTEERLVEHLLDPSRYNKLIRPATNGSELVTVQLMVSLAQLISVHEREQIMT
TNVWLTQEWEDYRLTWKPEEFDNMKKVRLPSKHIWLPDVVLYNNADGMYEVSFYSNAVVSYDGSIFWLPPAIYKSACK
IEVKHFPFDQQNCTMKLRSWTYDRTEIDLVLKSEVASLDDFTPSGEWDIVALPGRRNENPDDSTYVDITYDFIIRRKP
LFYTINLIIPCVLITSLAILAFYLPSDCGEKMTLCISVLLALTVFLLLISKIVPPTSLDVPLVGKYLMFTMVLVTFSI
VTSVCVLNVHHRSPTTHTMAPWVRHLVLDRTAWILCLGEQPMAHRPPATFQANKTDDCSGSDLLPAMGNHCSHVGGPQ
DLEKTPRGRGSPLPPPREASLAVRGLLQELSSIRHFLEKRDEMREVAEDWKYVAMVIDRLFLWIFVFVCVFGTIGMFL
QPLFQNYTTTTFLHSDHSAPSSK

FIG. 6

**cDNA Sequence of human nAChRβ4-mouse 5HT3 chimera
(SEQ ID NO:10)**

GGCACGAGCCGCCAGCAAACCTCGGGGGCCAGGACCGGCGCTCACTCGACCGCGCGGCTCACGGGTGCCCTGTGACCC
CACAGCGGAGCTCGCGGCGGCTGCCACCCGGCCCCGCCGGCCATGAGGCGCGCGCCTTCCCTGGTCCTTTTCTTCCTG
GTCGCCCTTTGCGGGCGCGGGAACTGCCGCGTGGCCAATGCGGAGGAAAAGCTGATGGACGACCTTCTGAACAAAACC
CGTTACAATAACCTGATCCGCCCAGCCACCAGCTCCTCACAGCTCATCTCCATCAAGCTGCAGCTCTCCCTGGCCCAG
CTTATCAGCGTGAATGAGCGAGAGCAGATCATGACCACCAATGTCTGGCTGAAACAGGAATGGACTGATTACCGCCTG
ACCTGGAACAGCTCCCGCTACGAGGGTGTGAACATCCTGAGGATCCCTGCAAAGCGCATCTGGTTGCCTGACATCGTG
CTTTACAACAACGCCGACGGGACCTATGAGGTGTCTGTCTACACCAACTTGATAGTCCGGTCCAACGGCAGCGTCCTG
TGGCTGCCCCCTGCCATCTACAAGAGCGCCTGCAAGATTGAGGTGAAGTACTTTCCCTTCGACCAGCAGAACTGCACC
CTCAAGTTCCGCTCCTGGACCTATGACCACACGGAGATAGACATGGTCCTCATGACGCCCACAGCCAGCATGGATGAC
TTTACTCCCAGTGGTGAGTGGGACATAGTGGCCCTCCCAGGGAGAAGGACAGTGAACCCACAAGACCCCAGCTACGTG
GACGTGACTTACGACTTCATCATCAAGCGCAAGCCTCTGTTCTACACCATCAACCTCATCATCCCCTGCGTGCTCACC
ACCTTGCTGGCCATCCTCGTCTTCTACCTGCCATCCGACTGCGGCGAGAAGATGACACTGTGCATCTCAGTGCTGCTG
GCACTGACATTCTTCCTGCTGCTCATCTCCAAGATCGTGCCACCCACCTCCCTCGATGTGCCTCTCATCGGCAAGTAC
CTCATGTTCACCATGGTGCTGGTCACCTTCTCCATCGTCACCAGCGTCTGTGTGCTCAATGTGCACCACCGCTCGCCC
AGCACCCACACCATGGCACCCTGGGTCAGGCACCTGGTCCTAGACAGAATAGCCTGGATACTCTGCCTAGGGGAGCAG
CCTATGGCCCATAGACCCCAGCCACCTTCCAAGCCAACAAGACTGATGACTGCTCAGGTTCTGATCTTCTTCCAGCC
ATGGGAAACCACTGCAGCCATGTTGGAGGACCTCAGGACTTGGAGAAGACCCAAGGGCAGAGGTAGCCCTCTTCCA
CCACCAAGGGAGGCCTCACTGGCTGTGCGTGGTCTCTTGCAAGAGCTATCCTCCATCCGCCACTTCCTGGAGAAGCGG
GATGAGATGCGGGAGGTGGCAGAGGACTGGAAGTACGTGGCTATGGTGGTGGACCGGCTGTTCCTGTGGGTGTTCATG
TTTGTGTGCGTCCTGGGCACTGTGGGGCTCTTCCTACCGCCCCTCTTCCAGACCCATGCAGCTTCTGAGGGGCCCTAC
GCTGCCCAGCGTGACTGAGGGCCCCCTGGGTTGTGGGGTGAGAGGATGTGAGTGGCCGGGTGGGCACTTTGCTGCTTC
TTTCTGGGTTGTGGCCGATGAGGCCCTAAGTAAATATGTGAGCATTGGCCATCAACCCCATCAAACCAGCCACAGCCG
TGGAACAGGCAAGGATGGGGGCCTGGGCTGTCCTCTCTGAATGCCTTGGAGGGATCCCAGGAAGCCCCAGTAGGAGGG
AGCTTCAGACAGTTCAATTCTGGCCTGTCTTCCTTCCCTGCACCGGGCAATGGGGATAAAGATGACTTCGTAGCAGCA
CCTACTATGCTTCAGGCATGGTGCCGGCCTGCCTCTCC

FIG. 7

**Protein Sequence of human nAChRβ4-mouse 5HT3 chimera
(SEQ ID NO:11)**

MRRAPSLVLFFLVALCGRGNCRVANAEEKLMDDLLNKTRYNNLIRPATSSSQLISIKLQLSLAQLISVNEREQIMTTN
VWLKQEWTDYRLTWNSSRYEGVNILRIPAKRIWLPDIVLYNNADGTYEVSVYTNLIVRSNGSVLWLPPAIYKSACKIE
VKYFPFDQQNCTLKFRSWTYDHTEIDMVLMTPTASMDDFTPSGEWDIVALPGRRTVNPQDPSYVDVTYDFIIKRKPLF
YTINLIIPCVLTTLLAILVFYLPSDCGEKMTLCISVLLALTFFLLLISKIVPPTSLDVPLIGKYLMFTMVLVTFSIVT
SVCVLNVHHRSPSTHTMAPWVRHLVLDRIAWILCLGEQPMAHRPPATFQANKTDDCSGSDLLPAMGNHCSHVGGPQDL
EKTPRGRGSPLPPPREASLAVRGLLQELSSIRHFLEKRDEMREVAEDWKYVAMVVDRLFLWVFMFVCVLGTVGLFLPP
LFQTHAASEGPYAAQRD

FIG. 8A putative M3 domains

| | | | |
|---|---|---|---|
| nAChR α4 | (see SEQ ID NO:1) | 304 | ELIGEYLLFTMIFVTLSIV |
| nAChR β2 | (see SEQ ID NO:2) | 295 | ELVGKYLMFTMVLVTFSIV |
| nAChR β4 | (see SEQ ID NO:3) | 293 | ELIGKYLMFTMVLVTFSIV |
| 5-HT3 | (see SEQ ID NO:4) | 303 | ELIGVYFVVCMALLVISLA |
| 5-HT3 (mur) | (see SEQ ID NO:5) | 306 | ELIGVYFVVCMALLVISLA |
| GABA-A R α3 | (see SEQ ID NO:12) | 337 | AM.DWFIAVCYAFVFSALI |
| GABA-A R β1 | (see SEQ ID NO:13) | 305 | AI.DIYLMGCFVFVFLALL |
| glyR α3 | (see SEQ ID NO:14) | 315 | AI.DIWMAVCLLFVFSALL |
| glyR β | (see SEQ ID NO:15) | 328 | AL.DVWLIACLLFGFASLV | putative C2 domains

| | | |
|---|---|---|
| nAChR α4 | 323 | ITVFVLNVHHRSPRTHTMPTWVRRVFLDIVPRLLLMKRPSVVKDNCRRL |
| nAChR β2 | 313 | TSVCVLNVHHRSPTTHTMAPWVKVVFLEKLPALLFMQQPRHHCARQR.L |
| nAChR β4 | 311 | TSVCVLNVHHRSPSTHTMAPWVKRCFLHTCLPTFLFMKRPGPDSSPARAF |
| 5-HT3 | 322 | ETIFIVRLVHKQDLQQPVPAWLRHLVLERIAWLLCLR............ |
| 5-HT3 (mur) | 325 | ETIFIVRLVHKQDLQRPVPDWLRHLVLDRIAWILCLG............ |
| GABA-A R α3 | 355 | EFATVNYF.........TKRSW..................AWEGKKV |
| GABA-A R β1 | 323 | EYAFVNYIFFGKGPQKKGA...SK.................QDQSANE |
| glyR α3 | 333 | EYAAVNFV....SRQHKELLRFRR................KRKNKTE |
| glyR β | 346 | EYAVVQVMLNNPKRVEAEKARIAK................AEQADGK |

FIG. 8B

```
nAChR α4     IESMHKMASAPRFWPEPEGEPPATSGTQSLHPPSPSFCVPLDVPAEPGPSCKSPSDQLPP
nAChR β2     ........RLRRRQREREGAGALFFREAPGADSCTCFVNRASVQGLAGAFGAEPA.....
nAChR β4     ........PPSKSCVTKPEATATSTSPSNFYGNSMYFVNPASAASKSPA.GSTPV.....
5-HT3        ............................................................
5-HT3 (mur)  ............................................................
GABA-A R α3  PEALEMKKKTP........AAPAKKTSTTFNIVGTTYPINL...................
GABA-A R β1  KNKLEMNKVQV........DAHGNILLSTLEIRNETSGSEV........LTSVSD....
glyR α3      AFALEKFYRFS........DMDDEVR........ESR.......................
glyR β       GGNVAKKNTVN........GTGTPVHISTLQV.GETRCKKV........CTSKSD....

nAChR α4     QQPLEAEKASPHPSPGPCRPPHGTQAPGLAKARSLSVQHMSSPGEAVEGGVRCRSRSIQY
nAChR β2     ..........................................PVAGP..GRS.....
nAChR β4     ..........................................AIPRDFWLRS.....
5-HT3        ......EQSTSQRPPATSQATKTDDCSAMGNHCS....HMGGPQDFEKS...........
5-HT3 (mur)  ......EQPMAHRPPATFQANKTDDCSAMGNTCS....HVGGPQDLEKT...........
GABA-A R α3  .........................AKDTEFSTIS..............KGA...
GABA-A R β1  .........................PKATMYSY.D..............SASIQY
glyR α3      .........................................................F
glyR β       .........................LRSNDFSIVG..............SLPRDF nAChR α4     CVPRDDAAPEADGQAAGALASRNTHSAELPPPDQPSPCKCTCKKEPSSVSPSATVKTRST
nAChR β2     ..........................GEPCGC.....................
nAChR β4     ..........................SGRFRQ.....................
5-HT3        ..PRDRCSP................PPPPREAS.....................
5-HT3 (mur)  ..PRGRGSP................LPPPREAS.....................
GABA-A R α3  .........................APSASST...................PTIIA
GABA-A R β1  ...RKP...........LSSREAYGRALD.RHGVPS..................KGRIR
glyR α3      .....S...........FTAYG.MGPCLQAKDGMTP..................KG..P
glyR β       .....E...........LSNYDCYGKPIEVNNGLGK..................SQ..A
```

FIG. 8C

| | | |
|---|---|---|
| nAChR α4 | 562 | KAPPPHLPLSPALTRAVEGVQYIADHLKAEDTDFSVKEDWKYVAMVIDR |
| nAChR β2 | 423 | ..........GLREAVDGVRFIADHMRSEDDDQSVSVDWKYVAMVIDR |
| nAChR β4 | 423 | ..........DVQEALEGVSFIAQHMKNDDEDQSVVEDWKYVAMVVDR |
| 5-HT3 | 413 | ......LAVC.GLLQELSSIR...QFLEKRDEIREVARDWLRVGSVLDK |
| 5-HT3 (mur) | 422 | ......LAVR.GLLQELSSIR...HFLEKRDEMREVARDWLRVGYVLDR |
| GABA-A R α3 | 433 | SPKATYVQDSPTETKT....Y...NSVSKVDK..............ISR |
| GABA-A R β1 | 431 | RRASQLKVKIPD..........LTDVNSIDK...............WSR |
| glyR α3 | 404 | NHPVQVMPKSPDEMRK....VFIDRAKKIDT...............ISR |
| glyR β | 454 | KNN.....KKPPPAKP....VIPTAAKRIDL................YAR | putative M4-E3 domains

| | | |
|---|---|---|
| nAChR α4 | 601 | IFLWMFIIVCLLGTVGLFLPPWLAGMI 627 |
| nAChR β2 | 461 | LFLWIFVFVCVFGTIGMFLQPLFQNYTTTTFLHSDHSAPSSK 502 |
| nAChR β4 | 461 | LFLWVFMFVCVLGTVGLFLPPLFQTHAASEGPYAAQRD 498 |
| 5-HT3 | 452 | LLFHIYLLAVLAYSITLVMLWSIWQYA 478 |
| 5-HT3 (mur) | 461 | LLFRIYLLAVLAYSITLVTLWSIWHYS 487 |
| GABA-A R α3 | 461 | II.FPVLFAIFNLVYWATYVNRESAIKGMIRKQ 492 |
| GABA-A R β1 | 455 | MF.FPITFSLFNVVYWLYYVH 475 |
| glyR α3 | 434 | ACFPLAFLIFNIFYWVIYKILRHEDIHHQQQD 465 |
| glyR β | 479 | ALFPFCFLFFNVIYWSIYL 497 |

FIG. 9
β2 chimera - <u>top</u> (See Figures 4 and 5);
α4 chimera - <u>bottom</u> (See Figures 2 and 3)
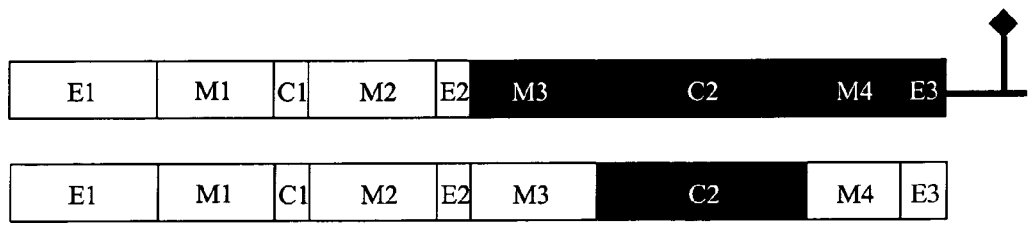

SEQUENCE LISTING

<160> NUMBER OF SEQ ID NOS: 15

<210> SEQ ID NO 1
<211> LENGTH: 627
<212> TYPE: PRT
<213> ORGANISM: Homo sapien

<400> SEQUENCE: 1

```
Met Glu Leu Gly Gly Pro Gly Ala Pro Arg Leu Leu Pro Leu Leu
 1               5                  10                  15

Leu Leu Leu Gly Thr Gly Leu Leu Arg Ala Ser Ser His Val Glu Thr
                20                  25                  30

Arg Ala His Ala Glu Glu Arg Leu Leu Lys Lys Leu Phe Ser Gly Tyr
             35                  40                  45

Asn Lys Trp Ser Arg Pro Val Ala Asn Ile Ser Asp Val Val Leu Val
         50                  55                  60

Arg Phe Gly Leu Ser Ile Ala Gln Leu Ile Asp Val Asp Glu Lys Asn
 65                  70                  75                  80

Gln Met Met Thr Thr Asn Val Trp Val Lys Gln Glu Trp His Asp Tyr
                 85                  90                  95

Lys Leu Arg Trp Asp Pro Ala Asp Tyr Glu Asn Val Thr Ser Ile Arg
            100                 105                 110

Ile Pro Ser Glu Leu Ile Trp Arg Pro Asp Ile Val Leu Tyr Asn Asn
            115                 120                 125

Ala Asp Gly Asp Phe Ala Val Thr His Leu Thr Lys Ala His Leu Phe
        130                 135                 140

His Asp Gly Arg Val Gln Trp Thr Pro Pro Ala Ile Tyr Lys Ser Ser
145                 150                 155                 160

Cys Ser Ile Asp Val Thr Phe Phe Pro Phe Asp Gln Gln Asn Cys Thr
                165                 170                 175

Met Lys Phe Gly Ser Trp Thr Tyr Asp Lys Ala Lys Ile Asp Leu Val
            180                 185                 190

Asn Met His Ser Arg Val Asp Gln Leu Asp Phe Trp Glu Ser Gly Glu
        195                 200                 205

Trp Val Ile Val Asp Ala Val Gly Thr Tyr Asn Thr Arg Lys Tyr Glu
    210                 215                 220

Cys Cys Ala Glu Ile Tyr Pro Asp Ile Thr Tyr Ala Phe Val Ile Arg
225                 230                 235                 240

Arg Leu Pro Leu Phe Tyr Thr Ile Asn Leu Ile Ile Pro Cys Leu Leu
                245                 250                 255

Ile Ser Cys Leu Thr Val Leu Val Phe Tyr Leu Pro Ser Glu Cys Gly
            260                 265                 270

Glu Lys Ile Thr Leu Cys Ile Ser Val Leu Leu Ser Leu Thr Val Phe
        275                 280                 285

Leu Leu Leu Ile Thr Glu Ile Ile Pro Ser Thr Ser Leu Val Ile Pro
    290                 295                 300

Leu Ile Gly Glu Tyr Leu Leu Phe Thr Met Ile Phe Val Thr Leu Ser
305                 310                 315                 320

Ile Val Ile Thr Val Phe Val Leu Asn Val His His Arg Ser Pro Arg
                325                 330                 335

Thr His Thr Met Pro Thr Trp Val Arg Arg Val Phe Leu Asp Ile Val
            340                 345                 350

Pro Arg Leu Leu Leu Met Lys Arg Pro Ser Val Val Lys Asp Asn Cys
```

```
                355                 360                 365
Arg Arg Leu Ile Glu Ser Met His Lys Met Ala Ser Ala Pro Arg Phe
    370                 375                 380

Trp Pro Glu Pro Glu Gly Glu Pro Pro Ala Thr Ser Gly Thr Gln Ser
385                 390                 395                 400

Leu His Pro Pro Ser Pro Ser Phe Cys Val Pro Leu Asp Val Pro Ala
                405                 410                 415

Glu Pro Gly Pro Ser Cys Lys Ser Pro Ser Asp Gln Leu Pro Pro Gln
            420                 425                 430

Gln Pro Leu Glu Ala Glu Lys Ala Ser Pro His Pro Ser Pro Gly Pro
        435                 440                 445

Cys Arg Pro Ser His Gly Thr Gln Ala Pro Gly Leu Ala Lys Ala Arg
    450                 455                 460

Ser Leu Ser Val Gln His Met Ser Ser Pro Gly Glu Ala Val Glu Gly
465                 470                 475                 480

Gly Val Arg Cys Arg Ser Arg Ser Ile Gln Tyr Cys Val Pro Arg Asp
                485                 490                 495

Asp Ala Pro Glu Ala Asp Gly Gln Ala Ala Gly Ala Leu Ala Ser
            500                 505                 510

Arg Asn Thr His Ser Ala Glu Leu Pro Pro Asp Gln Pro Ser Pro
        515                 520                 525

Cys Lys Cys Thr Cys Lys Lys Glu Pro Ser Ser Val Ser Pro Ser Ala
    530                 535                 540

Thr Val Lys Thr Arg Ser Thr Lys Ala Pro Pro His Leu Pro Leu
545                 550                 555                 560

Ser Pro Ala Leu Thr Arg Ala Val Glu Gly Val Gln Tyr Ile Ala Asp
                565                 570                 575

His Leu Lys Ala Glu Asp Thr Asp Phe Ser Val Lys Glu Asp Trp Lys
            580                 585                 590

Tyr Val Ala Met Val Ile Asp Arg Ile Phe Leu Trp Met Phe Ile Ile
        595                 600                 605

Val Cys Leu Leu Gly Thr Val Gly Leu Phe Leu Pro Pro Trp Leu Ala
    610                 615                 620

Gly Met Ile
625

<210> SEQ ID NO 2
<211> LENGTH: 502
<212> TYPE: PRT
<213> ORGANISM: Homo sapien

<400> SEQUENCE: 2

Met Ala Arg Arg Cys Gly Pro Val Ala Leu Leu Leu Gly Phe Gly Leu
1               5                   10                  15

Leu Arg Leu Cys Ser Gly Val Trp Gly Ala Asp Thr Glu Glu Arg Leu
            20                  25                  30

Val Glu His Leu Leu Asp Pro Ser Arg Tyr Asn Lys Leu Ile Arg Pro
        35                  40                  45

Ala Thr Asn Gly Ser Glu Leu Val Thr Val Gln Leu Met Val Ser Leu
    50                  55                  60

Ala Gln Leu Ile Ser Val His Glu Arg Glu Gln Ile Met Thr Thr Asn
65                  70                  75                  80

Val Trp Leu Thr Gln Glu Trp Glu Asp Tyr Arg Leu Thr Trp Lys Pro
                85                  90                  95
```

-continued

```
Glu Glu Phe Asp Asn Met Lys Lys Val Arg Leu Pro Ser Lys His Ile
            100                 105                 110

Trp Leu Pro Asp Val Val Leu Tyr Asn Asn Ala Asp Gly Met Tyr Glu
            115                 120                 125

Val Ser Phe Tyr Ser Asn Ala Val Val Ser Tyr Asp Gly Ser Ile Phe
            130                 135                 140

Trp Leu Pro Pro Ala Ile Tyr Lys Ser Ala Cys Lys Ile Glu Val Lys
145                 150                 155                 160

His Phe Pro Phe Asp Gln Gln Asn Cys Thr Met Lys Leu Arg Ser Trp
                165                 170                 175

Thr Tyr Asp Arg Thr Glu Ile Asp Leu Val Leu Lys Ser Glu Val Ala
            180                 185                 190

Ser Leu Asp Asp Phe Thr Pro Ser Gly Glu Trp Asp Ile Val Ala Leu
            195                 200                 205

Pro Gly Arg Arg Asn Glu Asn Pro Asp Asp Ser Thr Tyr Val Asp Ile
            210                 215                 220

Thr Tyr Asp Phe Ile Ile Arg Arg Lys Pro Leu Phe Tyr Thr Ile Asn
225                 230                 235                 240

Leu Ile Ile Pro Cys Val Leu Ile Thr Ser Leu Ala Ile Leu Ala Phe
                245                 250                 255

Tyr Leu Pro Ser Asp Cys Gly Glu Lys Met Thr Leu Cys Ile Ser Val
            260                 265                 270

Leu Leu Ala Leu Thr Val Phe Leu Leu Leu Ile Ser Lys Ile Val Pro
            275                 280                 285

Pro Thr Ser Leu Asp Val Pro Leu Val Gly Lys Tyr Leu Met Phe Thr
            290                 295                 300

Met Val Leu Val Thr Phe Ser Ile Val Thr Ser Val Cys Val Leu Asn
305                 310                 315                 320

Val His His Arg Ser Pro Thr Thr His Thr Met Ala Pro Trp Val Lys
                325                 330                 335

Val Val Phe Leu Glu Lys Leu Pro Ala Leu Leu Phe Met Gln Gln Pro
            340                 345                 350

Arg His His Cys Ala Arg Gln Arg Leu Arg Leu Arg Arg Gln Arg
                355                 360                 365

Glu Arg Glu Gly Ala Gly Ala Leu Phe Phe Arg Glu Ala Pro Gly Ala
            370                 375                 380

Asp Ser Cys Thr Cys Phe Val Asn Arg Ala Ser Val Gln Gly Leu Ala
385                 390                 395                 400

Gly Ala Phe Gly Ala Glu Pro Ala Pro Val Ala Gly Pro Gly Arg Ser
                405                 410                 415

Gly Glu Pro Cys Gly Cys Gly Leu Arg Glu Ala Val Asp Gly Val Arg
            420                 425                 430

Phe Ile Ala Asp His Met Arg Ser Glu Asp Asp Gln Ser Val Ser
            435                 440                 445

Val Asp Trp Lys Tyr Val Ala Met Val Ile Asp Arg Leu Phe Leu Trp
450                 455                 460

Ile Phe Val Phe Val Cys Val Phe Gly Thr Ile Gly Met Phe Leu Gln
465                 470                 475                 480

Pro Leu Phe Gln Asn Tyr Thr Thr Thr Phe Leu His Ser Asp His
                485                 490                 495

Ser Ala Pro Ser Ser Lys
            500
```

-continued

<210> SEQ ID NO 3
<211> LENGTH: 498
<212> TYPE: PRT
<213> ORGANISM: Homo sapien

<400> SEQUENCE: 3

Met Arg Arg Ala Pro Ser Leu Val Leu Phe Leu Val Ala Leu Cys
1               5                   10                  15

Gly Arg Gly Asn Cys Arg Val Ala Asn Ala Glu Glu Lys Leu Met Asp
            20                  25                  30

Asp Leu Leu Asn Lys Thr Arg Tyr Asn Asn Leu Ile Arg Pro Ala Thr
        35                  40                  45

Ser Ser Ser Gln Leu Ile Ser Ile Lys Leu Gln Leu Ser Leu Ala Gln
    50                  55                  60

Leu Ile Ser Val Asn Glu Arg Glu Gln Ile Met Thr Thr Asn Val Trp
65                  70                  75                  80

Leu Lys Gln Glu Trp Thr Asp Tyr Arg Leu Thr Trp Asn Ser Ser Arg
                85                  90                  95

Tyr Glu Gly Val Asn Ile Leu Arg Ile Pro Ala Lys Arg Ile Trp Leu
            100                 105                 110

Pro Asp Ile Val Leu Tyr Asn Asn Ala Asp Gly Thr Tyr Glu Val Ser
        115                 120                 125

Val Tyr Thr Asn Leu Ile Val Arg Ser Asn Gly Ser Val Leu Trp Leu
    130                 135                 140

Pro Pro Ala Ile Tyr Lys Ser Ala Cys Lys Ile Glu Val Lys Tyr Phe
145                 150                 155                 160

Pro Phe Asp Gln Gln Asn Cys Thr Leu Lys Phe Arg Ser Trp Thr Tyr
                165                 170                 175

Asp His Thr Glu Ile Asp Met Val Leu Met Thr Pro Thr Ala Ser Met
            180                 185                 190

Asp Asp Phe Thr Pro Ser Gly Glu Trp Asp Ile Ala Leu Pro Gly
        195                 200                 205

Arg Arg Thr Val Asn Pro Gln Asp Pro Ser Tyr Val Asp Val Thr Tyr
    210                 215                 220

Asp Phe Ile Ile Lys Arg Lys Pro Leu Phe Tyr Thr Ile Asn Leu Ile
225                 230                 235                 240

Ile Pro Cys Val Leu Thr Thr Leu Leu Ala Ile Leu Val Phe Tyr Leu
                245                 250                 255

Pro Ser Asp Cys Gly Glu Lys Met Thr Leu Cys Ile Ser Val Leu Leu
            260                 265                 270

Ala Leu Thr Phe Phe Leu Leu Leu Ile Ser Lys Ile Val Pro Pro Thr
        275                 280                 285

Ser Leu Asp Val Pro Leu Ile Gly Lys Tyr Leu Met Phe Thr Met Val
    290                 295                 300

Leu Val Thr Phe Ser Ile Val Thr Ser Val Cys Val Leu Asn Val His
305                 310                 315                 320

His Arg Ser Pro Ser Thr His Thr Met Ala Pro Trp Val Lys Arg Cys
                325                 330                 335

Phe Leu His Lys Leu Pro Thr Phe Leu Phe Met Lys Arg Pro Gly Pro
            340                 345                 350

Asp Ser Ser Pro Ala Arg Ala Phe Pro Pro Ser Lys Ser Cys Val Thr
        355                 360                 365

Lys Pro Glu Ala Thr Ala Thr Ser Thr Ser Pro Ser Asn Phe Tyr Gly
    370                 375                 380

```
Asn Ser Met Tyr Phe Val Asn Pro Ala Ser Ala Ala Ser Lys Ser Pro
385                 390                 395                 400

Ala Gly Ser Thr Pro Val Ala Ile Pro Arg Asp Phe Trp Leu Arg Ser
                405                 410                 415

Ser Gly Arg Phe Arg Gln Asp Val Gln Glu Ala Leu Glu Gly Val Ser
            420                 425                 430

Phe Ile Ala Gln His Met Lys Asn Asp Glu Asp Gln Ser Val Val
        435                 440                 445

Glu Asp Trp Lys Tyr Val Ala Met Val Val Asp Arg Leu Phe Leu Trp
450                 455                 460

Val Phe Met Phe Val Cys Val Leu Gly Thr Val Gly Leu Phe Leu Pro
465                 470                 475                 480

Pro Leu Phe Gln Thr His Ala Ala Ser Glu Gly Pro Tyr Ala Ala Gln
                485                 490                 495

Arg Asp
```

<210> SEQ ID NO 4
<211> LENGTH: 478
<212> TYPE: PRT
<213> ORGANISM: Homo sapien

<400> SEQUENCE: 4

```
Met Leu Leu Trp Val Gln Gln Ala Leu Leu Ala Leu Leu Leu Pro Thr
1               5                   10                  15

Leu Leu Ala Gln Gly Glu Ala Arg Arg Ser Arg Asn Thr Thr Arg Pro
            20                  25                  30

Ala Leu Leu Arg Leu Ser Asp Tyr Leu Leu Thr Asn Tyr Arg Lys Gly
        35                  40                  45

Val Arg Pro Val Arg Asp Trp Arg Lys Pro Thr Thr Val Ser Ile Asp
50                  55                  60

Val Ile Val Tyr Ala Ile Leu Asn Val Asp Glu Lys Asn Gln Val Leu
65                  70                  75                  80

Thr Thr Tyr Ile Trp Tyr Arg Gln Tyr Trp Thr Asp Glu Phe Leu Gln
                85                  90                  95

Trp Asn Pro Glu Asp Phe Asp Asn Ile Thr Lys Leu Ser Ile Pro Thr
            100                 105                 110

Asp Ser Ile Trp Val Pro Asp Ile Leu Ile Asn Glu Phe Val Asp Val
        115                 120                 125

Gly Lys Ser Pro Asn Ile Pro Tyr Val Tyr Ile Arg His Gln Gly Glu
130                 135                 140

Val Gln Asn Tyr Lys Pro Leu Gln Val Val Thr Ala Cys Ser Leu Asp
145                 150                 155                 160

Ile Tyr Asn Phe Pro Phe Asp Val Gln Asn Cys Ser Leu Thr Phe Thr
                165                 170                 175

Ser Trp Leu His Thr Ile Gln Asp Ile Asn Ile Ser Leu Trp Arg Leu
            180                 185                 190

Pro Glu Lys Val Lys Ser Asp Arg Ser Val Phe Met Asn Gln Gly Glu
        195                 200                 205

Trp Glu Leu Leu Gly Val Leu Pro Tyr Phe Arg Glu Phe Ser Met Glu
210                 215                 220

Ser Ser Asn Tyr Tyr Ala Glu Met Lys Phe Tyr Val Val Ile Arg Arg
225                 230                 235                 240

Arg Pro Leu Phe Tyr Val Val Ser Leu Leu Leu Pro Ser Ile Phe Leu
                245                 250                 255
```

```
Met Val Met Asp Ile Val Gly Phe Tyr Leu Pro Pro Asn Ser Gly Glu
            260                 265                 270

Arg Val Ser Phe Lys Ile Thr Leu Leu Gly Tyr Ser Val Phe Leu
        275                 280                 285

Ile Ile Val Ser Asp Thr Leu Pro Ala Thr Ala Ile Gly Thr Pro Leu
        290                 295                 300

Ile Gly Val Tyr Phe Val Val Cys Met Ala Leu Leu Val Ile Ser Leu
305                 310                 315                 320

Ala Glu Thr Ile Phe Ile Val Arg Leu Val His Lys Gln Asp Leu Gln
                325                 330                 335

Gln Pro Val Pro Ala Trp Leu Arg His Leu Val Leu Glu Arg Ile Ala
            340                 345                 350

Trp Leu Leu Cys Leu Arg Glu Gln Ser Thr Ser Gln Arg Pro Pro Ala
            355                 360                 365

Thr Ser Gln Ala Thr Lys Thr Asp Asp Cys Ser Ala Met Gly Asn His
        370                 375                 380

Cys Ser His Met Gly Gly Pro Gln Asp Phe Glu Lys Ser Pro Arg Asp
385                 390                 395                 400

Arg Cys Ser Pro Pro Pro Pro Arg Glu Ala Ser Leu Ala Val Cys
                405                 410                 415

Gly Leu Leu Gln Glu Leu Ser Ser Ile Arg Gln Phe Leu Glu Lys Arg
                420                 425                 430

Asp Glu Ile Arg Glu Val Ala Arg Asp Trp Leu Arg Val Gly Ser Val
                435                 440                 445

Leu Asp Lys Leu Leu Phe His Ile Tyr Leu Leu Ala Val Leu Ala Tyr
            450                 455                 460

Ser Ile Thr Leu Val Met Leu Trp Ser Ile Trp Gln Tyr Ala
465                 470                 475

<210> SEQ ID NO 5
<211> LENGTH: 483
<212> TYPE: PRT
<213> ORGANISM: Mouse

<400> SEQUENCE: 5

Met Arg Leu Cys Ile Pro Gln Val Leu Leu Ala Leu Phe Leu Ser Met
1               5                   10                  15

Leu Thr Ala Pro Gly Glu Gly Ser Arg Arg Ala Thr Gln Ala Arg
            20                  25                  30

Asp Thr Thr Gln Pro Ala Leu Leu Arg Leu Ser Asp His Leu Leu Ala
        35                  40                  45

Asn Tyr Lys Lys Gly Val Arg Pro Val Arg Asp Trp Arg Lys Pro Thr
    50                  55                  60

Thr Val Ser Ile Asp Val Ile Met Tyr Ala Ile Leu Asn Val Asp Glu
65                  70                  75                  80

Lys Asn Gln Val Leu Thr Thr Tyr Ile Trp Tyr Arg Gln Tyr Trp Thr
                85                  90                  95

Asp Glu Phe Leu Gln Trp Thr Pro Glu Asp Phe Asp Asn Val Thr Lys
            100                 105                 110

Leu Ser Ile Pro Thr Asp Ser Ile Trp Val Pro Asp Leu Ile Asn
        115                 120                 125

Glu Phe Val Asp Val Gly Lys Ser Pro Asn Ile Pro Tyr Val Tyr Val
130                 135                 140

His His Arg Gly Glu Val Gln Asn Tyr Lys Pro Leu Gln Leu Val Thr
145                 150                 155                 160
```

Ala Cys Ser Leu Asp Ile Tyr Asn Phe Pro Phe Asp Val Gln Asn Cys
            165                 170                 175

Ser Leu Thr Phe Thr Ser Trp Leu His Thr Ile Gln Asp Ile Asn Ile
        180                 185                 190

Thr Leu Trp Arg Ser Pro Glu Glu Val Arg Ser Asp Lys Ser Ile Phe
    195                 200                 205

Ile Asn Gln Gly Glu Trp Glu Leu Leu Glu Val Phe Pro Gln Phe Lys
210                 215                 220

Glu Phe Ser Ile Asp Ile Ser Asn Ser Tyr Ala Glu Met Lys Phe Tyr
225                 230                 235                 240

Val Ile Ile Arg Arg Arg Pro Leu Phe Tyr Ala Val Ser Leu Leu Leu
                245                 250                 255

Pro Ser Ile Phe Leu Met Val Val Asp Ile Val Gly Phe Cys Leu Pro
            260                 265                 270

Pro Asp Ser Gly Glu Arg Val Ser Phe Lys Ile Thr Leu Leu Leu Gly
        275                 280                 285

Tyr Ser Val Phe Leu Ile Ile Val Ser Asp Thr Leu Pro Ala Thr Ala
    290                 295                 300

Ile Gly Thr Pro Leu Ile Gly Val Tyr Phe Val Val Cys Met Ala Leu
305                 310                 315                 320

Leu Val Ile Ser Leu Ala Glu Thr Ile Phe Ile Val Arg Leu Val His
                325                 330                 335

Lys Gln Asp Leu Gln Arg Pro Val Pro Asp Trp Leu Arg His Leu Val
            340                 345                 350

Leu Asp Arg Ile Ala Trp Ile Leu Cys Leu Gly Glu Gln Pro Met Ala
        355                 360                 365

His Arg Pro Pro Ala Thr Phe Gln Ala Asn Lys Thr Asp Asp Cys Ser
    370                 375                 380

Ala Met Gly Asn Thr Cys Ser His Val Gly Gly Pro Gln Asp Leu Glu
385                 390                 395                 400

Lys Thr Pro Arg Gly Arg Gly Ser Pro Leu Pro Pro Arg Glu Ala
                405                 410                 415

Ser Leu Ala Val Arg Gly Leu Leu Gln Glu Leu Ser Ser Ile Arg His
            420                 425                 430

Phe Leu Glu Lys Arg Asp Glu Met Arg Glu Val Ala Arg Asp Trp Leu
        435                 440                 445

Arg Val Gly Tyr Val Leu Asp Arg Leu Leu Phe Arg Ile Tyr Leu Leu
    450                 455                 460

Ala Val Leu Ala Tyr Ser Ile Thr Leu Val Thr Leu Trp Ser Ile Trp
465                 470                 475                 480

His Tyr Ser

<210> SEQ ID NO 6
<211> LENGTH: 2130
<212> TYPE: DNA
<213> ORGANISM: Artificial Sequence
<220> FEATURE:
<223> OTHER INFORMATION: human nAChR alpha4-mouse 5HT3-FLAG chimera

<400> SEQUENCE: 6
ccatggagct agggggcccc ggagcgccgc ggctgctgcc gccgctgctg ctgcttctgg     60
ggaccggcct cctgcgcgcc agcagccatg tggagacccg ggcccacgcc gaggagcggc    120
tcctgaagaa actcttctcc ggttacaaca gtggtcccg accgtggcc aacatctcgg    180

-continued

```
acgtggtcct cgtccgcttc ggcctgtcca tcgctcagct cattgacgtg gatgagaaga        240
accagatgat gaccacgaac gtatgggtga agcaggagtg gcacgactac aagctgcgct        300
gggacccagc tgactatgag aatgtcacct ccatccgcat ccctccgag ctcatctggc         360 ggccggacat cgtcctctac aacaatgctg acggggactt cgcggtcacc cacctgacca        420
aggcccacct gttccatgac gggcgggtgc agtggactcc cccggccatt tacaagagct        480
cctgcagcat cgacgtcacc ttcttcccct cgaccagca gaactgcacc atgaaattcg        540
gctcctggac ctacgacaag gccaagatcg acctggtgaa catgcacagc cgcgtggacc        600
agctggactt ctgggagagt ggcgagtggg tcatcgtgga cgccgtgggc acctacaaca        660
ccaggaagta cgagtgctgc gccgagatct acccggacat cacctatgcc ttcgtcatcc        720
ggcggctgcc gctcttctac accatcaacc tcatcatccc ctgcctgctc atctcctgcc        780
tcaccgtgct ggtcttctac ctgcccctccg agtgcggcga aagatcacg ctgtgcatct         840 ccgtgctgct gtcgctcacc gtcttcctgc tgctcatcac cgagatcatc ccgtccacct        900
cactggtcat ccccctcatt ggtgtctact ttgtggtgtg catggctctg ctagtgataa        960
gcctcgctga ccatcttc attgtgcggc tggtgcataa gcaggaccta cagcggccag         1020
tacctgactg gctgaggcac ctggtcctag acagaatagc ctggatactc tgcctagggg       1080
agcagcctat ggcccataga cccccagcca ccttccaagc caacaagact gatgactgct       1140
caggttctga tcttcttcca gccatgggaa accactgcag ccatgttgga ggacctcagg       1200
acttggagaa gaccccaagg ggcagaggta gccctcttcc accaccaagg gaggcctcac       1260
tggctgtgcg tggtctcttg caagagctat cctccatccg ccacttcctg gagaagcggg       1320
atgagatgcg ggaggtggca agggactggc tgcgggtggg atacgtgctg acaggctgc        1380 tgttccgcat ctacctgctg gctgtgctcg cttacagcat caccctggtc actctctggt       1440
ccatttggca ttattctctc gaggattaca aggacgatga tgacaagtga gtctcaggca       1500
gggcgcatgc tcagagcagc tctcctgcct gcctctacag tgactgtgtc tcttgcctgc       1560
tggttgtgat ccctggatac tcgggcgttt gtgtcaccct acaaccctg tccccgctgt       1620 gactcatttg ggttgtgctg gccttccctg ggtctctttc tcccaagcct tgggtgttac        1680
gtacagactt tcgactgaga gctggatggc tgtgcctgat accacccat ccccatggca        1740 ccacttggcc tcctggcctc cagacagata gccctattcc atccctaat ggtgagccaa        1800 cctgcacaga cacataggg cacggagccc tcaggatgca agggtccct catcagtcca         1860 ggagttcttg gtcacgcctt ggaggaagat ggcaatgggt tctctcctag aaggggatat        1920
tgcttatgga acatacccga ctccgctggc agggacagtc aggaagatgc tgctgtcacc       1980
ctttgtccag cctctccagt gagtattcag gaaactcagt tggccttacc tgggccatct       2040
caaaggttcc aggataaccc ccactctcct agcctccacc ctcctaaaca ctctcctccc       2100
ccagccctgt tggcacagca tagctctaga                                         2130
```

<210> SEQ ID NO 7
<211> LENGTH: 495
<212> TYPE: PRT
<213> ORGANISM: Artificial Sequence
<220> FEATURE:
<223> OTHER INFORMATION: human nAChR alpha4-mouse 5HT3-FLAG chimera

<400> SEQUENCE: 7

Met Glu Leu Gly Gly Pro Gly Ala Pro Arg Leu Leu Pro Pro Leu Leu
1               5                   10                  15

-continued

```
Leu Leu Leu Gly Thr Gly Leu Leu Arg Ala Ser Ser His Val Glu Thr
         20                  25                  30

Arg Ala His Ala Glu Glu Arg Leu Leu Lys Lys Leu Phe Ser Gly Tyr
         35                  40                  45

Asn Lys Trp Ser Arg Pro Val Ala Asn Ile Ser Asp Val Val Leu Val
 50                  55                  60

Arg Phe Gly Leu Ser Ile Ala Gln Leu Ile Asp Val Asp Glu Lys Asn
 65                  70                  75                  80

Gln Met Met Thr Thr Asn Val Trp Val Lys Gln Glu Trp His Asp Tyr
                 85                  90                  95

Lys Leu Arg Trp Asp Pro Ala Asp Tyr Glu Asn Val Thr Ser Ile Arg
             100                 105                 110

Ile Pro Ser Glu Leu Ile Trp Arg Pro Asp Ile Val Leu Tyr Asn Asn
         115                 120                 125

Ala Asp Gly Asp Phe Ala Val Thr His Leu Thr Lys Ala His Leu Phe
130                 135                 140

His Asp Gly Arg Val Gln Trp Thr Pro Pro Ala Ile Tyr Lys Ser Ser
145                 150                 155                 160

Cys Ser Ile Asp Val Thr Phe Phe Pro Phe Asp Gln Gln Asn Cys Thr
                 165                 170                 175

Met Lys Phe Gly Ser Trp Thr Tyr Asp Lys Ala Lys Ile Asp Leu Val
             180                 185                 190

Asn Met His Ser Arg Val Asp Gln Leu Asp Phe Trp Glu Ser Gly Glu
         195                 200                 205

Trp Val Ile Val Asp Ala Val Gly Thr Tyr Asn Thr Arg Lys Tyr Glu
210                 215                 220

Cys Cys Ala Glu Ile Tyr Pro Asp Ile Thr Tyr Ala Phe Val Ile Arg
225                 230                 235                 240

Arg Leu Pro Leu Phe Tyr Thr Ile Asn Leu Ile Ile Pro Cys Leu Leu
                 245                 250                 255

Ile Ser Cys Leu Thr Val Leu Val Phe Tyr Leu Pro Ser Glu Cys Gly
             260                 265                 270

Glu Lys Ile Thr Leu Cys Ile Ser Val Leu Leu Ser Leu Thr Val Phe
         275                 280                 285

Leu Leu Leu Ile Thr Glu Ile Ile Pro Ser Thr Ser Leu Val Ile Pro
290                 295                 300

Leu Ile Gly Val Tyr Phe Val Cys Met Ala Leu Leu Val Ile Ser
305                 310                 315                 320

Leu Ala Glu Thr Ile Phe Ile Val Arg Leu Val His Lys Gln Asp Leu
                 325                 330                 335

Gln Arg Pro Val Pro Asp Trp Leu Arg His Leu Val Leu Asp Arg Ile
             340                 345                 350

Ala Trp Ile Leu Cys Leu Gly Glu Gln Pro Met Ala His Arg Pro Pro
         355                 360                 365

Ala Thr Phe Gln Ala Asn Lys Thr Asp Asp Cys Ser Gly Ser Asp Leu
370                 375                 380

Leu Pro Ala Met Gly Asn His Cys Ser His Val Gly Gly Pro Gln Asp
385                 390                 395                 400

Leu Glu Lys Thr Pro Arg Gly Arg Gly Ser Pro Leu Pro Pro Pro Arg
                 405                 410                 415

Glu Ala Ser Leu Ala Val Arg Gly Leu Leu Gln Glu Leu Ser Ser Ile
             420                 425                 430

Arg His Phe Leu Glu Lys Arg Asp Glu Met Arg Glu Val Ala Arg Asp
```

```
                435             440             445
Trp Leu Arg Val Gly Tyr Val Leu Asp Arg Leu Leu Phe Arg Ile Tyr
    450             455             460

Leu Leu Ala Val Leu Ala Tyr Ser Ile Thr Leu Val Thr Leu Trp Ser
465             470             475             480

Ile Trp His Tyr Ser Leu Glu Asp Tyr Lys Asp Asp Asp Lys
            485             490             495

<210> SEQ ID NO 8
<211> LENGTH: 1496
<212> TYPE: DNA
<213> ORGANISM: Artificial Sequence
<220> FEATURE:
<223> OTHER INFORMATION: human nAChR beta2-mouse 5HT3 chimera

<400> SEQUENCE: 8
ctgcccgcgg catggcccgg cgctgcggcc ccgtggcgct gctccttggc ttcggcctcc       60
tccggctgtg ctcaggggtg tggggtgcgg atacagagga gcggctggtg gagcatctcc      120
tggatccttc ccgctacaac aagcttatcc gcccagccac caatggctct gagctggtga      180
cagtacagct tatggtgtca ctggcccagc tcatcagtgt gcatgagcgg gagcagatca      240
tgaccaccaa tgtctggctg acccaggagt gggaagatta cgcctcacc tggaagcctg       300 aagagtttga caacatgaag aaagttcggc tcccttccaa acacatctgg ctcccagatg      360
tggtcctgta caacaatgct gacggcatgt acgaggtgtc cttctattcc aatgccgtgg      420
tctcctatga tggcagcatc ttctggctgc gcctgccat ctacaagagc gcatgcaaga      480
ttgaagtaaa gcacttccca tttgaccagc agaactgcac catgaagctc cgttcgtgga      540
cctacgaccg cacagagatc gacttggtgc tgaagagtga ggtggccagc ctagacgact      600
tcacacctag tggtgagtgg gacatcgtgg cgctgccggg ccggcgcaac gagaaccccg      660
acgactctac gtacgtggac atcacgtatg acttcatcat cgccgcaag ccgctcttct       720 acaccatcaa cctcatcatc cctgtgtgc tcatcacctc gctagccatc cttgccttct      780
acctgccatc cgactgtggc gagaagatga cgttgtgcat ctcagtgctg ctggcgctca      840
cggtcttcct gctgctcatc tccaagatcg tgcctcccac ctccctcgac gtgccgctcg      900
tcggcaagta cctcatgttc accatggtgc ttgtcacctt ctccatcgtc accagcgtgt      960
gcgtgctcaa cgtgcaccac cgctcgccca ccacgcacac catggcgccc tgggtgaggc     1020
acctggtcct agacagaata gcctggatac tctgcctagg ggagcagcct atggcccata     1080 gaccccagc caccttccaa gccaacaaga ctgatgactg ctcaggttct gatcttcttc     1140
cagccatggg aaaccactgc agccatgttg gaggacctca ggacttggag aagacccca      1200 ggggcagagg tagccctctt ccaccaccaa gggaggcctc actggctgtg cgtggtctct     1260
tgcaagagct atcctccatc cgccacttcc tggagaagcg ggatgagatg cgggaggtgg     1320
cagaggactg gaagtacgtc gccatggtga tcgaccgcct cttcctctgg atctttgtct     1380
ttgtctgtgt ctttggcacc atcggcatgt tcctgcagcc tctcttccag aactacacca     1440
ccaccacctt cctccactca gaccactcag ccccagctc caagtgaggc ccttcc         1496

<210> SEQ ID NO 9
<211> LENGTH: 491
<212> TYPE: PRT
<213> ORGANISM: Artificial Sequence
<220> FEATURE:
<223> OTHER INFORMATION: human nAChR beta2-mouse 5HT3 chimera
```

<400> SEQUENCE: 9

```
Met Ala Arg Arg Cys Gly Pro Val Ala Leu Leu Leu Gly Phe Gly Leu
 1               5                  10                  15

Leu Arg Leu Cys Ser Gly Val Trp Gly Ala Asp Thr Glu Glu Arg Leu
             20                  25                  30

Val Glu His Leu Leu Asp Pro Ser Arg Tyr Asn Lys Leu Ile Arg Pro
         35                  40                  45

Ala Thr Asn Gly Ser Glu Leu Val Thr Val Gln Leu Met Val Ser Leu
     50                  55                  60

Ala Gln Leu Ile Ser Val His Glu Arg Glu Gln Ile Met Thr Thr Asn
 65                  70                  75                  80

Val Trp Leu Thr Gln Glu Trp Glu Asp Tyr Arg Leu Thr Trp Lys Pro
                 85                  90                  95

Glu Glu Phe Asp Asn Met Lys Lys Val Arg Leu Pro Ser Lys His Ile
            100                 105                 110

Trp Leu Pro Asp Val Val Leu Tyr Asn Asn Ala Asp Gly Met Tyr Glu
        115                 120                 125

Val Ser Phe Tyr Ser Asn Ala Val Val Ser Tyr Asp Gly Ser Ile Phe
    130                 135                 140

Trp Leu Pro Pro Ala Ile Tyr Lys Ser Ala Cys Lys Ile Glu Val Lys
145                 150                 155                 160

His Phe Pro Phe Asp Gln Gln Asn Cys Thr Met Lys Leu Arg Ser Trp
                165                 170                 175

Thr Tyr Asp Arg Thr Glu Ile Asp Leu Val Leu Lys Ser Glu Val Ala
            180                 185                 190

Ser Leu Asp Asp Phe Thr Pro Ser Gly Glu Trp Asp Ile Val Ala Leu
        195                 200                 205

Pro Gly Arg Arg Asn Glu Asn Pro Asp Asp Ser Thr Tyr Val Asp Ile
    210                 215                 220

Thr Tyr Asp Phe Ile Ile Arg Arg Lys Pro Leu Phe Tyr Thr Ile Asn
225                 230                 235                 240

Leu Ile Ile Pro Cys Val Leu Ile Thr Ser Leu Ala Ile Leu Ala Phe
                245                 250                 255

Tyr Leu Pro Ser Asp Cys Gly Glu Lys Met Thr Leu Cys Ile Ser Val
            260                 265                 270

Leu Leu Ala Leu Thr Val Phe Leu Leu Leu Ile Ser Lys Ile Val Pro
        275                 280                 285

Pro Thr Ser Leu Asp Val Pro Leu Val Gly Lys Tyr Leu Met Phe Thr
    290                 295                 300

Met Val Leu Val Thr Phe Ser Ile Val Thr Ser Val Cys Val Leu Asn
305                 310                 315                 320

Val His His Arg Ser Pro Thr Thr His Thr Met Ala Pro Trp Val Arg
                325                 330                 335

His Leu Val Leu Asp Arg Ile Ala Trp Ile Leu Cys Leu Gly Glu Gln
            340                 345                 350

Pro Met Ala His Arg Pro Pro Ala Thr Phe Gln Ala Asn Lys Thr Asp
        355                 360                 365

Asp Cys Ser Gly Ser Asp Leu Leu Pro Ala Met Gly Asn His Cys Ser
    370                 375                 380

His Val Gly Gly Pro Gln Asp Leu Glu Lys Thr Pro Arg Gly Arg Gly
385                 390                 395                 400

Ser Pro Leu Pro Pro Arg Glu Ala Ser Leu Ala Val Arg Gly Leu
                405                 410                 415
```

```
Leu Gln Glu Leu Ser Ser Ile Arg His Phe Leu Glu Lys Arg Asp Glu
            420                 425                 430

Met Arg Glu Val Ala Glu Asp Trp Lys Tyr Val Ala Met Val Ile Asp
        435                 440                 445

Arg Leu Phe Leu Trp Ile Phe Val Phe Val Cys Val Phe Gly Thr Ile
    450                 455                 460

Gly Met Phe Leu Gln Pro Leu Phe Gln Asn Tyr Thr Thr Thr Thr Phe
465                 470                 475                 480

Leu His Ser Asp His Ser Ala Pro Ser Ser Lys
                485                 490

<210> SEQ ID NO 10
<211> LENGTH: 1910
<212> TYPE: DNA
<213> ORGANISM: Artificial Sequence
<220> FEATURE:
<223> OTHER INFORMATION: human nAChR beta4-mouse 5HT3 chimera

<400> SEQUENCE: 10
ggcacgagcc gccagcaaac ctcgggggcc aggaccggcg ctcactcgac cgcgcggctc      60
acgggtgccc tgtgacccca cagcggagct cgcggcggct gccacccggc ccgccggcc     120 atgaggcgcg cgccttccct ggtccttttc ttcctggtcg ccctttgcgg gcgcgggaac     180
tgccgcgtgg ccaatgcgga ggaaaagctg atggacgacc ttctgaacaa aacccgttac     240
aataacctga tccgcccagc caccagctcc tcacagctca tctccatcaa gctgcagctc     300
tccctggccc agcttatcag cgtgaatgag cgagagcaga tcatgaccac caatgtctgg     360
ctgaaacagg aatggactga ttaccgcctg acctggaaca gctcccgcta cgagggtgtg     420
aacatcctga ggatccctgc aaagcgcatc tggttgcctg acatcgtgct ttacaacaac     480
gccgacggga cctatgaggt gtctgtctac accaacttga tagtccggtc aacggcagc     540 gtcctgtggc tgccccctgc catctacaag agcgcctgca gattgaggt gaagtacttt     600 cccttcgacc agcagaactg caccctcaag ttccgctcct ggacctatga ccacacggag     660
atagacatgg tcctcatgac gcccacagcc agcatggatg actttactcc cagtggtgag     720
tgggacatag tggccctccc agggagaagg acagtgaacc cacaagaccc cagctacgtg     780
gacgtgactt acgacttcat catcaagcgc aagcctctgt tctacaccat caacctcatc     840
atcccctgcg tgctcaccac cttgctggcc atcctcgtct tctacctgcc atccgactgc     900
ggcgagaaga tgacactgtg catctcagtg ctgctggcac tgacattctt cctgctgctc     960
atctccaaga tcgtgccacc cacctccctc gatgtgcctc tcatcggcaa gtacctcatg    1020
ttcaccatgg tgctggtcac cttctccatc gtcaccagcg tctgtgtgct caatgtgcac    1080
caccgctcgc ccagcaccca ccatggca cctgggtca ggcacctggt cctagacaga    1140
atagcctgga tactctgcct aggggagcag cctatgccc atagacccc agccaccttc    1200 caagccaaca gactgatga ctgctcaggt tctgatcttc ttccagccat gggaaaccac    1260
tgcagccatg ttggaggacc tcaggacttg gagaagaccc aaggggcag aggtagccct    1320 cttccaccac caagggaggc ctcactggct gtgcgtggtc tcttgcaaga gctatcctcc    1380
atccgccact tcctggagaa gcgggatgag atgcgggagg tggcagagga ctggaagtac    1440
gtggctatgg tggtggaccg gctgttcctg tgggtgttca tgttttgtgtg cgtcctgggc    1500 actgtggggc tcttcctacc gcccctcttc cagacccatg cagcttctga ggggccctac    1560
gctgcccagc gtgactgagg gccccctggg ttgtggggtg agaggatgtg agtggccggg    1620
```

-continued

```
tgggcacttt gctgcttctt tctgggttgt ggccgatgag gccctaagta aatatgtgag    1680
cattggccat caaccccatc aaaccagcca cagccgtgga acaggcaagg atgggggcct    1740
gggctgtcct ctctgaatgc cttggaggga tcccaggaag ccccagtagg agggagcttc    1800
agacagttca attctggcct gtcttccttc cctgcaccgg gcaatgggga taaagatgac    1860
ttcgtagcag cacctactat gcttcaggca tggtgccggc ctgcctctcc              1910
```

<210> SEQ ID NO 11
<211> LENGTH: 485
<212> TYPE: PRT
<213> ORGANISM: Artificial Sequence
<220> FEATURE:
<223> OTHER INFORMATION: human nAChR beta4-mouse 5HT3 chimera

<400> SEQUENCE: 11

```
Met Arg Arg Ala Pro Ser Leu Val Leu Phe Phe Leu Val Ala Leu Cys
  1               5                  10                  15

Gly Arg Gly Asn Cys Arg Val Ala Asn Ala Glu Glu Lys Leu Met Asp
                 20                  25                  30

Asp Leu Leu Asn Lys Thr Arg Tyr Asn Asn Leu Ile Arg Pro Ala Thr
             35                  40                  45

Ser Ser Ser Gln Leu Ile Ser Ile Lys Leu Gln Leu Ser Leu Ala Gln
         50                  55                  60

Leu Ile Ser Val Asn Glu Arg Glu Gln Ile Met Thr Thr Asn Val Trp
 65                  70                  75                  80

Leu Lys Gln Glu Trp Thr Asp Tyr Arg Leu Thr Trp Asn Ser Ser Arg
                 85                  90                  95

Tyr Glu Gly Val Asn Ile Leu Arg Ile Pro Ala Lys Arg Ile Trp Leu
            100                 105                 110

Pro Asp Ile Val Leu Tyr Asn Asn Ala Asp Gly Thr Tyr Glu Val Ser
        115                 120                 125

Val Tyr Thr Asn Leu Ile Val Arg Ser Asn Gly Ser Val Leu Trp Leu
    130                 135                 140

Pro Pro Ala Ile Tyr Lys Ser Ala Cys Lys Ile Glu Val Lys Tyr Phe
145                 150                 155                 160

Pro Phe Asp Gln Gln Asn Cys Thr Leu Lys Phe Arg Ser Trp Thr Tyr
                165                 170                 175

Asp His Thr Glu Ile Asp Met Val Leu Met Thr Pro Thr Ala Ser Met
            180                 185                 190

Asp Asp Phe Thr Pro Ser Gly Glu Trp Asp Ile Val Ala Leu Pro Gly
        195                 200                 205

Arg Arg Thr Val Asn Pro Gln Asp Pro Ser Tyr Val Asp Val Thr Tyr
    210                 215                 220

Asp Phe Ile Ile Lys Arg Lys Pro Leu Phe Tyr Thr Ile Asn Leu Ile
225                 230                 235                 240

Ile Pro Cys Val Leu Thr Thr Leu Leu Ala Ile Leu Val Phe Tyr Leu
                245                 250                 255

Pro Ser Asp Cys Gly Glu Lys Met Thr Leu Cys Ile Ser Val Leu Leu
            260                 265                 270

Ala Leu Thr Phe Phe Leu Leu Leu Ile Ser Lys Ile Val Pro Pro Thr
        275                 280                 285

Ser Leu Asp Val Pro Leu Ile Gly Lys Tyr Leu Met Phe Thr Met Val
    290                 295                 300

Leu Val Thr Phe Ser Ile Val Thr Ser Val Cys Val Leu Asn Val His
```

```
                305                 310                 315                 320
His Arg Ser Pro Ser Thr His Thr Met Ala Pro Trp Val Arg His Leu
                325                 330                 335

Val Leu Asp Arg Ile Ala Trp Ile Leu Cys Leu Gly Glu Gln Pro Met
                340                 345                 350

Ala His Arg Pro Pro Ala Thr Phe Gln Ala Asn Lys Thr Asp Asp Cys
                355                 360                 365

Ser Gly Ser Asp Leu Leu Pro Ala Met Gly Asn His Cys Ser His Val
                370                 375                 380

Gly Gly Pro Gln Asp Leu Glu Lys Thr Pro Arg Gly Arg Gly Ser Pro
385                 390                 395                 400

Leu Pro Pro Pro Arg Glu Ala Ser Leu Ala Val Arg Gly Leu Leu Gln
                405                 410                 415

Glu Leu Ser Ser Ile Arg His Phe Leu Glu Lys Arg Asp Glu Met Arg
                420                 425                 430

Glu Val Ala Glu Asp Trp Lys Tyr Val Ala Met Val Val Asp Arg Leu
                435                 440                 445

Phe Leu Trp Val Phe Met Phe Val Cys Val Leu Gly Thr Val Gly Leu
                450                 455                 460

Phe Leu Pro Pro Leu Phe Gln Thr His Ala Ala Ser Glu Gly Pro Tyr
465                 470                 475                 480

Ala Ala Gln Arg Asp
                485

<210> SEQ ID NO 12
<211> LENGTH: 492
<212> TYPE: PRT
<213> ORGANISM: Homo sapien

<400> SEQUENCE: 12

Met Ile Ile Thr Gln Thr Ser His Cys Tyr Met Thr Ser Leu Gly Ile
1               5                   10                  15

Leu Phe Leu Ile Asn Ile Leu Pro Gly Thr Thr Gly Gln Gly Glu Ser
                20                  25                  30

Arg Arg Gln Glu Pro Gly Asp Phe Val Lys Gln Asp Ile Gly Gly Leu
                35                  40                  45

Ser Pro Lys His Ala Pro Asp Ile Pro Asp Asp Ser Thr Asp Asn Ile
                50                  55                  60

Thr Ile Phe Thr Arg Ile Leu Asp Arg Leu Leu Asp Gly Tyr Asp Asn
65                  70                  75                  80

Arg Leu Arg Pro Gly Leu Gly Asp Ala Val Thr Glu Val Lys Thr Asp
                85                  90                  95

Ile Tyr Val Thr Ser Phe Gly Pro Val Ser Asp Thr Asp Met Glu Tyr
                100                 105                 110

Thr Ile Asp Val Phe Phe Arg Gln Thr Trp His Asp Glu Arg Leu Lys
                115                 120                 125

Phe Asp Gly Pro Met Lys Ile Leu Pro Leu Asn Asn Leu Leu Ala Ser
                130                 135                 140

Lys Ile Trp Thr Pro Asp Thr Phe Phe His Asn Gly Lys Lys Ser Val
145                 150                 155                 160

Ala His Asn Met Thr Thr Pro Asn Lys Leu Leu Arg Leu Val Asp Asn
                165                 170                 175

Gly Thr Leu Pro Tyr Thr Met Arg Leu Thr Ile His Ala Glu Cys Pro
                180                 185                 190
```

```
Met His Leu Glu Asp Phe Pro Met Asp Val His Ala Cys Pro Leu Lys
        195                 200                 205

Phe Gly Ser Tyr Ala Tyr Thr Thr Ala Glu Val Val Tyr Ser Trp Thr
210                 215                 220

Leu Gly Lys Asn Lys Ser Val Glu Val Ala Gln Asp Gly Ser Arg Leu
225                 230                 235                 240

Asn Gln Tyr Asp Leu Leu Gly His Val Gly Thr Glu Ile Ile Arg
                245                 250                 255

Ser Ser Thr Gly Glu Tyr Val Val Met Thr Thr His Phe His Leu Lys
                260                 265                 270

Arg Lys Ile Gly Tyr Phe Val Ile Gln Thr Tyr Leu Pro Cys Ile Met
                275                 280                 285

Thr Val Ile Leu Ser Gln Val Ser Phe Trp Leu Asn Arg Glu Ser Val
        290                 295                 300

Pro Ala Arg Thr Val Phe Gly Val Thr Thr Val Leu Thr Met Thr Thr
305                 310                 315                 320

Leu Ser Ile Ser Ala Arg Asn Ser Leu Pro Lys Val Ala Tyr Ala Thr
                325                 330                 335

Ala Met Asp Trp Phe Ile Ala Val Cys Tyr Ala Phe Val Phe Ser Ala
                340                 345                 350

Leu Ile Glu Phe Ala Thr Val Asn Tyr Phe Thr Lys Arg Ser Trp Ala
        355                 360                 365

Trp Glu Gly Lys Lys Val Pro Glu Ala Leu Glu Met Lys Lys Lys Thr
    370                 375                 380

Pro Ala Ala Pro Ala Lys Lys Thr Ser Thr Thr Phe Asn Ile Val Gly
385                 390                 395                 400

Thr Thr Tyr Pro Ile Asn Leu Ala Lys Asp Thr Glu Phe Ser Thr Ile
                405                 410                 415

Ser Lys Gly Ala Ala Pro Ser Ala Ser Ser Thr Pro Thr Ile Ile Ala
                420                 425                 430

Ser Pro Lys Ala Thr Tyr Val Gln Asp Ser Pro Thr Glu Thr Lys Thr
                435                 440                 445

Tyr Asn Ser Val Ser Lys Val Asp Lys Ile Ser Arg Ile Ile Phe Pro
        450                 455                 460

Val Leu Phe Ala Ile Phe Asn Leu Val Tyr Trp Ala Thr Tyr Val Asn
465                 470                 475                 480

Arg Glu Ser Ala Ile Lys Gly Met Ile Arg Lys Gln
                485                 490

<210> SEQ ID NO 13
<211> LENGTH: 474
<212> TYPE: PRT
<213> ORGANISM: Homo sapien

<400> SEQUENCE: 13

Met Trp Thr Val Gln Asn Arg Glu Ser Leu Gly Leu Leu Ser Phe Pro
1               5                   10                  15

Val Met Ile Thr Met Val Cys Cys Ala His Ser Thr Asn Glu Pro Ser
            20                  25                  30

Asn Met Ser Tyr Val Lys Glu Thr Val Asp Arg Leu Leu Lys Gly Tyr
        35                  40                  45

Asp Ile Arg Leu Arg Pro Asp Phe Gly Gly Pro Pro Val Asp Val Gly
    50                  55                  60

Met Arg Ile Asp Val Ala Ser Ile Asp Met Val Ser Glu Val Asn Met
65                  70                  75                  80
```

```
Asp Tyr Thr Leu Thr Met Tyr Phe Gln Gln Ser Trp Lys Asp Lys Arg
                85                  90                  95

Leu Ser Tyr Ser Gly Ile Pro Leu Asn Leu Thr Leu Asp Asn Arg Val
            100                 105                 110

Ala Asp Gln Leu Cys Val Pro Asp Thr Tyr Phe Leu Asn Asp Lys Lys
        115                 120                 125

Ser Phe Val His Gly Val Thr Val Lys Asn Arg Met Ile Arg Leu His
    130                 135                 140

Pro Asp Gly Thr Val Leu Tyr Gly Leu Arg Ile Thr Thr Thr Ala Ala
145                 150                 155                 160

Cys Met Met Asp Leu Arg Arg Tyr Pro Leu Asp Glu Gln Asn Cys Thr
                165                 170                 175

Leu Glu Ile Glu Ser Tyr Gly Tyr Thr Thr Asp Asp Ile Glu Phe Tyr
            180                 185                 190

Trp Asn Gly Gly Glu Gly Ala Val Thr Gly Val Asn Lys Ile Glu Leu
        195                 200                 205

Pro Gln Phe Ser Ile Val Asp Tyr Lys Met Val Ser Lys Lys Val Glu
    210                 215                 220

Phe Thr Thr Gly Ala Tyr Pro Arg Leu Ser Leu Ser Phe Arg Leu Lys
225                 230                 235                 240

Arg Asn Ile Gly Tyr Phe Ile Leu Gln Thr Tyr Met Pro Ser Thr Leu
                245                 250                 255

Ile Thr Ile Leu Ser Trp Val Ser Phe Trp Ile Asn Tyr Asp Ala Ser
            260                 265                 270

Ala Ala Arg Val Ala Leu Gly Ile Thr Thr Val Leu Thr Met Thr Thr
        275                 280                 285

Ile Ser Thr His Leu Arg Glu Thr Leu Pro Lys Ile Pro Tyr Val Lys
    290                 295                 300

Ala Ile Asp Ile Tyr Leu Met Gly Cys Phe Val Phe Val Phe Leu Ala
305                 310                 315                 320

Leu Leu Glu Tyr Ala Phe Val Asn Tyr Ile Phe Phe Gly Lys Gly Pro
                325                 330                 335

Gln Lys Lys Gly Ala Ser Lys Gln Asp Gln Ser Ala Asn Glu Lys Asn
            340                 345                 350

Lys Leu Glu Met Asn Lys Val Gln Val Asp Ala His Gly Asn Ile Leu
        355                 360                 365

Leu Ser Thr Leu Glu Ile Arg Asn Glu Thr Ser Gly Ser Glu Val Leu
    370                 375                 380

Thr Ser Val Ser Asp Pro Lys Ala Thr Met Tyr Ser Tyr Asp Ser Ala
385                 390                 395                 400

Ser Ile Gln Tyr Arg Lys Pro Leu Ser Ser Arg Glu Ala Tyr Gly Arg
                405                 410                 415

Ala Leu Asp Arg His Gly Val Pro Ser Lys Gly Arg Asn Arg Arg
            420                 425                 430

Ala Ser Gln Leu Lys Val Lys Ile Pro Asp Leu Thr Asp Val Asn Ser
        435                 440                 445

Ile Asp Lys Trp Ser Arg Met Phe Phe Pro Ile Thr Phe Ser Leu Phe
    450                 455                 460

Asn Val Val Tyr Trp Leu Tyr Tyr Val His
465                 470

<210> SEQ ID NO 14
<211> LENGTH: 465
```

<212> TYPE: PRT
<213> ORGANISM: Homo sapien

<400> SEQUENCE: 14

```
Met Ala His Val Arg His Phe Arg Thr Leu Val Ser Gly Phe Tyr Phe
 1               5                  10                  15

Trp Glu Ala Ala Leu Leu Leu Ser Leu Val Ala Thr Lys Glu Thr Asp
                 20                  25                  30

Ser Ala Arg Ser Arg Ser Ala Pro Met Ser Pro Ser Asp Phe Leu Asp
             35                  40                  45

Lys Leu Met Gly Arg Thr Ser Gly Tyr Asp Ala Arg Ile Arg Pro Asn
 50                  55                  60

Phe Lys Gly Pro Pro Val Asn Val Thr Cys Asn Ile Phe Ile Asn Ser
 65                  70                  75                  80

Phe Gly Ser Ile Ala Glu Thr Thr Met Asp Tyr Arg Val Asn Ile Phe
                 85                  90                  95

Leu Arg Gln Lys Trp Asn Asp Pro Arg Leu Ala Tyr Ser Glu Tyr Pro
            100                 105                 110

Asp Asp Ser Leu Asp Leu Asp Pro Ser Met Leu Asp Ser Ile Trp Lys
        115                 120                 125

Pro Asp Leu Phe Phe Ala Asn Glu Lys Gly Ala Asn Phe His Glu Val
130                 135                 140

Thr Thr Asp Asn Lys Leu Leu Arg Ile Phe Lys Asn Gly Asn Val Leu
145                 150                 155                 160

Tyr Ser Ile Arg Leu Thr Leu Thr Leu Ser Cys Pro Met Asp Leu Lys
                165                 170                 175

Asn Phe Pro Met Asp Val Gln Thr Cys Ile Met Gln Leu Glu Ser Phe
            180                 185                 190

Gly Tyr Thr Met Asn Asp Leu Ile Phe Glu Trp Gln Asp Glu Ala Pro
        195                 200                 205

Val Gln Val Ala Glu Gly Leu Thr Leu Pro Gln Phe Leu Leu Lys Glu
210                 215                 220

Glu Lys Asp Leu Arg Tyr Cys Thr Lys His Tyr Asn Thr Gly Lys Phe
225                 230                 235                 240

Thr Cys Ile Glu Val Arg Phe His Leu Glu Arg Gln Met Gly Tyr Tyr
                245                 250                 255

Leu Ile Gln Met Tyr Ile Pro Ser Leu Leu Ile Val Ile Leu Ser Trp
            260                 265                 270

Val Ser Phe Trp Ile Asn Met Asp Ala Ala Pro Ala Arg Val Ala Leu
        275                 280                 285

Gly Ile Thr Thr Val Leu Thr Met Thr Thr Gln Ser Ser Gly Ser Arg
290                 295                 300

Ala Ser Leu Pro Lys Val Ser Tyr Val Lys Ala Ile Asp Ile Trp Met
305                 310                 315                 320

Ala Val Cys Leu Leu Phe Val Phe Ser Ala Leu Leu Glu Tyr Ala Ala
                325                 330                 335

Val Asn Phe Val Ser Arg Gln His Lys Glu Leu Leu Arg Phe Arg Arg
            340                 345                 350

Lys Arg Lys Asn Lys Thr Glu Ala Phe Ala Leu Glu Lys Phe Tyr Arg
        355                 360                 365

Phe Ser Asp Met Asp Asp Glu Val Arg Glu Ser Arg Phe Ser Phe Thr
370                 375                 380

Ala Tyr Gly Met Gly Pro Cys Leu Gln Ala Lys Asp Gly Met Thr Pro
385                 390                 395                 400
```

```
Lys Gly Pro Asn His Pro Val Gln Val Met Pro Lys Ser Pro Asp Glu
            405                 410                 415

Met Arg Lys Val Phe Ile Asp Arg Ala Lys Lys Ile Asp Thr Ile Ser
        420                 425                 430

Arg Ala Cys Phe Pro Leu Ala Phe Leu Ile Phe Asn Ile Phe Tyr Trp
        435                 440                 445

Val Ile Tyr Lys Ile Leu Arg His Glu Asp Ile His His Gln Gln Gln
        450                 455                 460

Asp
465

<210> SEQ ID NO 15
<211> LENGTH: 497
<212> TYPE: PRT
<213> ORGANISM: Homo sapien

<400> SEQUENCE: 15

Met Lys Phe Leu Leu Thr Thr Ala Phe Leu Ile Leu Ile Ser Leu Trp
  1               5                  10                  15

Val Glu Glu Ala Tyr Ser Lys Glu Lys Ser Ser Lys Lys Gly Lys Gly
             20                  25                  30

Lys Lys Lys Gln Tyr Leu Cys Pro Ser Gln Gln Ser Ala Glu Asp Leu
         35                  40                  45

Ala Arg Val Pro Ala Asn Ser Thr Ser Asn Ile Leu Asn Arg Leu Leu
     50                  55                  60

Val Ser Tyr Asp Pro Arg Ile Arg Pro Asn Phe Lys Gly Ile Pro Val
 65                  70                  75                  80

Asp Val Val Val Asn Ile Phe Ile Asn Ser Phe Gly Ser Ile Gln Glu
                 85                  90                  95

Thr Thr Met Asp Tyr Arg Val Asn Ile Phe Leu Arg Gln Lys Trp Asn
            100                 105                 110

Asp Pro Arg Leu Lys Leu Pro Ser Asp Phe Arg Gly Ser Asp Ala Leu
        115                 120                 125

Thr Val Asp Pro Thr Met Tyr Lys Cys Leu Trp Lys Pro Asp Leu Phe
130                 135                 140

Phe Ala Asn Glu Lys Ser Ala Asn Phe His Asp Val Thr Gln Glu Asn
145                 150                 155                 160

Ile Leu Leu Phe Ile Phe Arg Asp Gly Asp Val Leu Val Ser Met Arg
                165                 170                 175

Leu Ser Ile Thr Leu Ser Cys Pro Leu Asp Leu Thr Leu Phe Pro Met
            180                 185                 190

Asp Thr Gln Arg Cys Lys Met Gln Leu Glu Ser Phe Gly Tyr Thr Thr
        195                 200                 205

Asp Asp Leu Arg Phe Ile Trp Gln Ser Gly Asp Pro Val Gln Leu Glu
    210                 215                 220

Lys Ile Ala Leu Pro Gln Phe Asp Ile Lys Lys Glu Asp Ile Glu Tyr
225                 230                 235                 240

Gly Asn Cys Thr Lys Tyr Tyr Lys Gly Thr Gly Tyr Tyr Thr Cys Val
                245                 250                 255

Glu Val Ile Phe Thr Leu Arg Arg Gln Val Gly Phe Tyr Met Met Gly
            260                 265                 270

Val Tyr Ala Pro Thr Leu Leu Ile Val Val Leu Ser Trp Leu Ser Phe
        275                 280                 285

Trp Ile Asn Pro Asp Ala Ser Ala Ala Arg Val Pro Leu Gly Ile Phe
```

-continued

```
            290                 295                 300
Ser Val Leu Ser Leu Ala Ser Glu Cys Thr Thr Leu Ala Ala Glu Leu
305                 310                 315                 320

Pro Lys Val Ser Tyr Val Lys Ala Leu Asp Val Trp Leu Ile Ala Cys
                325                 330                 335

Leu Leu Phe Gly Phe Ala Ser Leu Val Glu Tyr Ala Val Val Gln Val
                340                 345                 350

Met Leu Asn Asn Pro Lys Arg Val Glu Ala Glu Lys Ala Arg Ile Ala
                355                 360                 365

Lys Ala Glu Gln Ala Asp Gly Lys Gly Asn Val Ala Lys Lys Asn
                370                 375                 380

Thr Val Asn Gly Thr Gly Thr Pro Val His Ile Ser Thr Leu Gln Val
385                 390                 395                 400

Gly Glu Thr Arg Cys Lys Lys Val Cys Thr Ser Lys Ser Asp Leu Arg
                405                 410                 415

Ser Asn Asp Phe Ser Ile Val Gly Ser Leu Pro Arg Asp Phe Glu Leu
                420                 425                 430

Ser Asn Tyr Asp Cys Tyr Gly Lys Pro Ile Glu Val Asn Asn Gly Leu
                435                 440                 445

Gly Lys Ser Gln Ala Lys Asn Asn Lys Lys Pro Pro Pro Ala Lys Pro
        450                 455                 460

Val Ile Pro Thr Ala Ala Lys Arg Ile Asp Leu Tyr Ala Arg Ala Leu
465                 470                 475                 480

Phe Pro Phe Cys Phe Leu Phe Phe Asn Val Ile Tyr Trp Ser Ile Tyr
                485                 490                 495

Leu
```

CHIMERIC NICOTINIC RECEPTOR SUBUNITS

This application is a continuation of international Application No. PCT/US03/22550, filed on Jul. 18, 2003, which claims the benefit of U.S. Provisional Application No. 60/397,380, filed Jul. 19, 2002, now abandoned.

FIELD OF THE INVENTION

The present invention relates to novel chimeric nicotinic acetylcholine receptor (nAChR) subunits. Isolated nucleic acid molecules are provided encoding chimeric nAChR subunits based on substituted human nAChR subunits, including chimeric human α4, β2, and β4 nAChR subunits. Chimeric nAChR subunit polypeptides are also provided, as are vectors, host cells and recombinant methods for producing the same. The invention further relates to screening methods for identifying modulators of nAChR activity using the chimeric subunits of the invention.

BACKGROUND

Each nAChR subtype is a homo- or hetero-pentameric assembly of distinct subunits. Subunit N-terminal domains contribute to ligand recognition, and second transmembrane domains lining the ion channel contribute to channel kinetics and ion selectivity. Large, second cytoplasmic domains (C2) contain sequences that are unique to each subunit including possible phosphorylation sites implicated in nAChR desensitization.

Exploration of nAChR subunit function in receptor activity is important in order to further understand modulation and possible control of receptor function in vivo. Nicotine has been proposed to have a number of pharmacological effects. See, for example, Pullan et al., *N. Engl. J. Med.* 330:811 (1994). Certain of those effects can be related to effects upon neurotransmitter release. See, for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992).

Confirmatory reports and additional recent studies have included the modulation in the Central Nervous System (CNS) of glutamate, nitric oxide, GABA, takykinins, cytokines and peptides (reviewed in Brioni et al., *Adv. Pharmacol.* 37:153 (1997)). In addition, nicotine reportedly potentiates the pharmacological behavior of certain pharmaceutical compositions used for the treatment of certain disorders. See, for example, Sanberg et al., *Pharmacol. Biochem. & Behavior* 46:303 (1993), Harsing et al., *J. Neurochem.* 59:48 (1993) and Hughes, Proceedings from Intl. Symp. Nic. S40 (1994). Furthermore, various other beneficial pharmacological effects of nicotine have been proposed. See, for example, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *J. Pharmacol. Exp. Ther.* 221:91(1982); and Hamon, *Trends in Pharmacol. Res.* 15:36 (1994).

Various nicotinic compounds have been reported as being useful for treating a wide variety of conditions and disorders. See, for example, Williams et al., *Drug News Perspec.* 7(4): 205 (1994); Arneric et al., *CNS Drug Rev.* 1(1):1 (1995); Arneric et al., *Exp. Opin. Invest. Drugs* 5(1):79 (1996); Bencherif et al., *J. Pharmacol. Exp. Ther.* 279:1413 (1996); Lippiello et al., *J. Pharmacol. Exp. Ther.* 279:1422 (1996); Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); Holladay et al., *J. Med. Chem.* 40(28):4169 (1997); Bannon et al., *Science* 279: 77 (1998); PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al. Nicotinic compounds are reported as being particularly useful for treating a wide variety of CNS disorders. Indeed, a wide variety of compounds have been reported to have therapeutic properties. See, for example, U.S. Pat. No. 5,187,166 to Kikuchi et al.; U.S. Pat. No. 5,672,601 to Cignarella; PCT WO 99/21834; PCT WO 97/40049; UK Patent Application GB 2295387; and European Patent Application 297,858.

CNS disorders are a type of neurological disorder. Several CNS disorders can be attributed to a deficiency of acetylcholine, dopamine, norepinephrine and/or serotonin. CNS disorders can be drug-induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Relatively common CNS disorders include pre-senile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, progressive supranuclear palsy, Huntington's chorea, tardive dyskinesia, hyperkinesia, mania, attention deficit disorder, anxiety, dyslexia, schizophrenia, depression, obsessive-compulsive disorders and Tourette's syndrome.

It is desirable to provide methods for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to effect the functioning of the CNS, but, when employed in an amount sufficient to effect the functioning of the CNS, does not significantly effect those receptor subtypes which have the potential to induce undesirable side effects (e.g., appreciable activity at cardiovascular and skeletal muscle sites). The discovery and development of such compositions and methods depends on knowledge of receptor activity, including ligand-modulation of receptor activity through ligand interaction with the receptor or specific subunits thereof.

Accordingly, there is a need for further elucidation of nAChR activity and the modulation thereof. Modified receptor subunits provide additional means to explore modulation of receptor activity. Therefore, there is a need for identification and characterization of modified receptor subunits.

SUMMARY OF THE INVENTION

The present invention provides isolated nucleic acid molecules comprising a polynucleotide encoding the chimeric nAChR subunit polypeptides having the amino acid sequence shown in FIG. 3, 5, or 7 (SEQ ID NOS: 7, 9, or 11, respectively), or any other sequence according to the present invention.

The present invention also relates to recombinant vectors, which include the isolated nucleic acid molecules of the present invention, and to host cells containing the recombinant vectors, as well as to methods of making such vectors and host cells and for using them for production of chimeric nAChR subunit polypeptides or peptides by recombinant techniques.

The invention further provides an isolated chimeric nAChR subunit polypeptide having an amino acid sequence encoded by a polynucleotide described herein.

The present invention also provides a screening method for identifying compounds capable of enhancing or inhibiting a cellular response mediated by a chimeric nAChR subunit, which involves contacting cells which express a chimeric nAChR subunit with the candidate compound, assaying a cellular response, and comparing the cellular response to a standard cellular response, the standard response being assayed when contact is made in absence of the candidate compound; whereby, an increased cellular response over the standard indicates that the compound is an agonist and a decreased cellular response over the standard indicates that the compound is an antagonist, i.e. for the function measured by the assay.

As used herein the term "chimeric nAChR subunit" polypeptide includes human nAChR subunits having a substitution of an non-naturally occurring sequence in the region of the polypeptide including at least a part of a second, large cytoplasmic domain (C2).

Accordingly, in one aspect, the invention relates to a polypeptide comprising a chimeric human nAChR receptor subunit having a substitution of at least a portion of the C-terminal cytoplasmic domain, wherein the substitution comprises at least about 15% of the native amino acid sequence of the subunit. The substitution can also comprise at least about 20% of the native amino acid sequence of the subunit. The substitution can also comprise at least a portion of a transmembrane domain adjacent to the C-terminal end of the cytoplasmic domain.

In one embodiment, the substitution further comprises all of the transmembrane domain C-terminal to the large, C-terminal cytoplasmic domain and at least a portion of a C-terminal extracellular domain. In other embodiments, the substitution further comprises at least a portion of a transmembrane domain adjacent to the N-terminal end of the cytoplasmic domain. In still further embodiments, the substitution comprises all of the C-terminal cytoplasmic domain and at least a portion of each transmembrane domain positioned adjacent to the cytoplasmic domain. In another embodiment, the substitution further comprises all of the transmembrane domains adjacent to the cytoplasmic domain and all native subunit amino acids C-terminal to the cytoplasmic domain.

The substituted sequence can be characteristic of domains that are structurally analogous to those being replaced in the native nAChR polypeptide and can be derived from a receptor subunit of a ligand-gated ion channel superfamily receptor. The receptor subunit from which the substituted sequence is derived can be characterized by having four transmembrane domains. The subunit can be from a receptor selected from the group consisting of GABA-A, glycine, seratonin, and nAChR receptors. The receptor can be a homopentameric receptor. The substituted sequence can be derived from a nAChR receptor subunit. The nAChR receptor subunit can be an α7 nAChR subunit. The substituted sequence can also be derived from a subunit of a serotonin type 3 receptor. The substituted sequence can also be derived from a subunit selected from the group consisting of GABA-A R α3, GABA-A R β1, glyR α3, and glyR β.

In another aspect, the invention relates to a polynucleotide encoding the polypeptide disclosed herein or a polypeptide having conservative amino acid substitutions thereof. In one embodiment, the polynucleotide is DNA.

In another aspect, the invention relates to a method of making a vector comprising inserting the polynucleotide of the invention into a vector.

In another aspect, the invention relates to a vector produced by the method of the invention.

In another aspect, the invention relates to a method of making a host cell comprising introducing the vector of the invention into a host cell.

In another aspect, the invention relates to a host cell produced by the method of the invention.

In another aspect, the invention relates to an isolated polypeptide of the invention, produced by a method comprising: (a) introducing a vector comprising a polynucleotide encoding the polypeptide into a host cell; (b) culturing the host cell; and (c) recovering the polypeptide.

In another aspect, the invention relates to a method for producing a polypeptide comprising: (a) culturing the host cell of the invention under conditions that the vector is expressed; and (b) recovering the polypeptide.

In another aspect, the invention relates to cells containing at least one polynucleotide of the invention, wherein said cells are bacterial cells, eukaryotic cells or amphibian oocytes. In one embodiment of the invention, the cells further contain at least one polynucleotide encoding a second subunit of human nAChR, wherein the subunit can be a chimeric or native amino acid sequence and is a α subunit if the first subunit is a β subunit and is a β subunit if the first subunit is an α subunit. The cells can be further characterized as being capable of expressing voltage dependent calcium channels. Also, the cells can be characterized as expressing functional nAChR that contain one or more subunits encoded by the polynucleotide.

In another aspect, the invention relates to a method of screening compounds to identify compounds which modulate the activity of human neuronal nAChR. The method comprises determining the effect of a compound on the neuronal nAChR activity in test cells, compared to the effect on control cells or to the neuronal nAChR activity of the cells in the absence of the compound, wherein control cells are substantially identical to the test cells, but control cells do not express nAChR.

In another aspect, the invention relates to a method of screening compounds to identify compounds which modulate the activity of human neuronal nAChR, said method comprising determining the effect of a compound on the neuronal nAChR activity in test cells compared to the effect on control cells or to the neuronal nAChR activity of the cells in the absence of the compound, wherein control cells are substantially identical to the test cells, but control cells do not express nAChR.

It will be recognized that compounds screened according to methods of the present invention can be characterized as agonists, antagonists, or partial agonists based on evaluation of their interaction with nAChR comprising the chimeric subunits of the invention. Also, compounds can be screened on the basis of their binding or more limited functional effects such that candidates for further evaluation are determined. In this aspect, the methods of the invention can provide an initial screen for compounds that may be further evaluated based on other experiments. The invention provides methods for characterization of compounds as agonists, antagonists, or partial agonists, as well as methods for initial selection of candidate compounds for further evaluation.

In another aspect, the invention relates to a polynucleotide encoding a human nAChR α4 subunit comprising a substitution of at least a portion of the large C-terminal cytoplasmic domain, the substitution comprising at least about 15% of the native amino acid sequence of the subunit. The substitution can comprise at least about 20% of the native sequence. In one embodiment, the substitution of the subunit begins in a region encoding from about amino acid position number P304 to about amino acid position number S362 of SEQ ID NO: 1 and ends in a region beginning from about amino acid number P562 to about I627 of SEQ ID NO:1. In another embodiment, the substitution of the subunit begins in a region encoding from about amino acid position number H331 to about amino acid position number L355 of SEQ ID NO: 1 and ends in a region beginning from about amino acid number R566 to about R600 of SEQ ID NO:1.

In another aspect, the invention relates to a polynucleotide encoding a human nAChR β2 subunit comprising a substitution of at least a portion of the large C-terminal cytoplasmic domain, the substitution comprising at least about 15% of the native amino acid sequence of the subunit. The substitution can comprise at least about 20% of the native sequence. In one embodiment, the substitution of the subunit begins in a region encoding from about amino acid position number P295 to about amino acid position number R353 of SEQ ID NO: 2 and ends in a region beginning from about amino acid number C422 to about K502 of SEQ ID NO:2. In another embodiment, the substitution of the subunit begins in a region encoding from about amino acid position number H322 to about amino acid position number Q350 of SEQ ID NO: 2 and ends in a region beginning from about amino acid number E426 to about R460 of SEQ ID NO:2.

In another aspect, the invention relates to a polynucleotide encoding a human nAChR β4 subunit comprising a substitution of at least about 15% of the native amino acid sequence of the subunit large C-terminal cytoplasmic domain. The substitution can comprise at least about 20% of the native sequence. In one embodiment, the substitution of the subunit begins in a region encoding from about amino acid position number P293 to about amino acid position number G351 of SEQ ID NO: 3 and ends in a region beginning from about amino acid number Q422 to about D498 of SEQ ID NO:3. In another embodiment, the substitution of the subunit begins in a region encoding from about amino acid position number H320 to about amino acid position number K348 of SEQ ID NO: 3 and ends in a region beginning from about amino acid number E426 to about R460 of SEQ ID NO:3.

In will be recognized that the amino acid positions above, noted with respect to the particular sequences disclosed herein, will have appropriate counterpart positions in homologous regions of related subunits. Accordingly, one of skill in the art will be able to use this guidance in selecting appropriate positioning for other substitutions according to the invention disclosed herein.

BRIEF DESCRIPTION OF THE FIGURES

FIGS. 1A and 1B show a tentative alignment of the amino acid sequences of human α4, β2, and β4 (SEQ ID NOS: 1, 2, and 3, respectively) nAChR subunits with each other, and with human (SEQ ID NO: 4) and mouse (SEQ ID NO: 5) 5HT3R serotonin type 3 receptor subunits.

FIG. 2 shows a nucleotide sequence comprising the encoding sequence of one example of a human nAChR α4-mouse 5HT3-FLAG chimera (SEQ ID NO: 6) (polypeptide sequence of the chimera is shown in FIG. 3).

FIG. 3 shows an amino acid sequence of one example of a human nAChR α4-mouse 5HT3-FLAG chimera of the invention (SEQ ID NO: 7).

FIG. 4 shows a nucleotide sequence comprising the encoding sequence of one example of a human nAChR β2-mouse 5HT3 chimera (SEQ ID NO:8) (polypeptide sequence of the chimera shown in FIG. 5).

FIG. 5 shows an amino acid sequence of one example of a human nAChR β2-mouse 5HT3 chimera of the invention (SEQ ID NO: 9).

FIG. 6 shows a nucleotide sequence comprising the encoding sequence of one example of a human nAChR β4-mouse 5HT3 chimera (SEQ ID NO: 10) (polypeptide sequence of the chimera shown in FIG. 7).

FIG. 7 shows an amino acid sequence of one example of a human nAChR β4-mouse 5HT3 chimera of the invention (SEQ ID NO: 11).

FIGS. 8A-8C show putative M3, C2 and M4-E3 domains, respectively, of receptor subunits of nicotinic acetylcholine receptors and of receptor subunits that can donate substituted sequences to form chimeric receptor subunits according to particular embodiments of the invention. Dark shading shows potential start sites for the chimeric substitution, while the lighter shading shows potential stop sites for the substitution. Polypeptide sequences for the domains shown correspond to the indicated sequences as shown in SEQ ID NOS: 1-5 (nAChR α4, β2, β4, human 5-HT3, and murine 5-HT3, respectively), and SEQ ID NOS: 12-15 (GABA-A R α3 and β1, glyR α3 and β, respectively).

FIG. 9 shows schematic diagrams of β2 and α4 chimeric receptor subunits according to two examples of the invention. The diagrams illustrate the basic structure of the subunits of the invention: E1, E2, and E3 are the extracellular subunit domains, from the most N-terminal domain to the most C-terminal domain, respectively; M1-M4 are the transmembrane domains; and C1 and C2 are the cytoplasmic domains.

DETAILED DESCRIPTION

Figure 10:
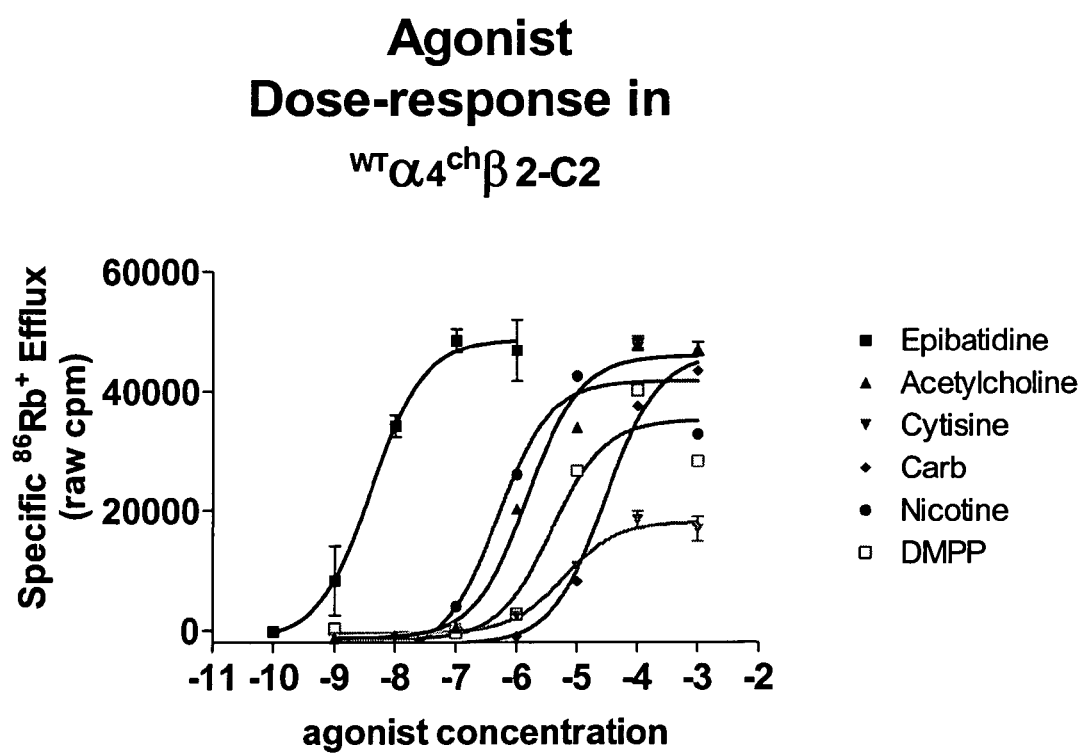
FIG. 10 shows a graphic representation of agonist dose response of a receptor comprising a wild type α4/chimeric β2 subunit according to one embodiment of the present invention (see the amino acid sequence as shown in FIG. 5 (SEQ ID NO:9)). Carb=carbamylcholine; DMPP=dimethyl phenyl piperazinium. See Example 3, C.

Nicotinic AChR are diverse members of the ligand-gated ion channel superfamily (Lukas, R. J., *Neuronal nicotinic acetylcholine receptors*, in *The Nicotinic Acetylcholine Receptors: Current Views and Future Trends*, F. J. Barrantes, Editor., Springer Verlag, Berlin/Heidelberg and Landes Publishing: Georgetown, Tex. p. 145-173 (1998)). Each nAChR subtype is a pentamer assembled as a unique combination of diverse subunits encoded by a member of a family of at least 17 genes. Each of the nAChR subunits has a conserved structure including an extracellular N-terminal domain, four transmembrane domains (M1-M4), a large cytoplasmic loop located between the M3 and M4 domains, and an extracellular C-terminus. Sequences and structural elements involved in ligand recognition are embedded in the extracellular N-terminal domain (Devillers-Thiery, A., et al., *J Membr Biol.*, 136(2):97-112 (1993)) and the small extracellular loop between M2 and M3 transmembrane domains (Campos-Caro, A., et al., *Proc Natl Acad Sci USA*, 93(12):6118-23 (1996)). Furthermore, the M2 transmembrane domain is thought to form the lining of the ion-channel.

Without wishing to be bound by any particular theory, it appears that the structural characteristics of receptors comprising the chimeric subunits relate to their functional characteristics in a manner that is partially predictable based on preserved or substituted domains of the particular chimera. The chimeras of the invention preserve the first extracellular domain involved in subunit assembly and ligand recognition. These chimeras preserve the drug-binding properties of the native receptors. Also, the first and second transmembrane domains, and even the short loop between M2 and M3, preserve gating characteristics of the channel (lined by M2 and— in part, at least in the "vestibule" region on the extracellular face by M1 sequences) and transduction of ligand binding to channel opening (believed to involve interactions between the external domain, the short M2-M3 loop, and the external surfaces of the channel). In the chimeric subunits of the invention, the artificially introduced cytoplasmic +/−M3/M4 sequences can confer unique properties to the engineered subunits of the source subunit. Among these might be selective targeting of the subunit to specific cellular domains, specific interactions with cytoplasmic or cytoskeletal proteins that could be used to help purify the chimeric receptors or subunits, and any unique functional properties.

In FIGS. 8A-8C, protein sequences from the third transmembrane domain through to the C-terminus are aligned for human nicotinic acetylcholine receptor (nAChR) α4, β2, and β4 subunits, human and mouse (mur) serotonergic 5-HT3 subunits (5-HT3), human γ-amino butyric acid A receptor (GABA-A R) α3 and β1 subunits, and human glycine receptor (glyR) α3 and β subunits. Amino acid residue numbering makes reference to the translation initiation methionine as residue 1. Sequences from these proteins are representative of those that can be used to generate chimeric subunits, assembly of which can produce novel receptors having ligand binding and ion channel properties dictated by N-terminal extracellular and first and second transmembrane domains but that can have novel features dictated by third and fourth transmembrane domains and the second, major, cytoplasmic loop.

Potential starting positions for splicing sequences from one subunit into another are indicated by the dark shading, and potential stopping positions for such insertions are indicated by light shading in FIGS. 8A-8C. For example, substitution for the nAChR α4 sequence starting at the beginning of the M3 domain (P304) could be effected using sequences starting at the corresponding amino acid residue of other subunits (e.g., P295 from the nAChR β subunit, P303 from the human 5-HT3 subunit, or A315 from the glyR α3 subunit). Substitution for the nAChR α4 sequence starting anywhere in the C2 domain bordering M3 (e.g., from I323 to S362) could be effected using sequences starting at the corresponding amino acid residues of other subunits (e.g., from T313 to S352 for the nAChR β2 subunit, from E322 to R358 for the human 5-HT3 subunit, or from E333 to R352 for the glyR α3 subunit). As other examples, aside from continuing the substitution all the way through to the C-terminal residue, substitution for the nAChR α4 sequence ending anywhere in the C2 domain bordering M4 (e.g., from P572 to R600) could be effected using sequences starting at the corresponding amino acid residues of other subunits (e.g., from G423 to R460 for the nAChR β2 subunit, from G417 to R451 for the human 5-HT3 subunit, or from P414 to R433 for the glyR α3 subunit).

In one example of the present invention, the substituted sequence is derived from a serotonin type 3 receptor (5HT3R). The 5HT3R receptors are also members of the ligand-gated ion channel superfamily, and share extensive sequence similarity and, also likely, structural homology with nAChR (Maricq, A. V., et al., *Science*, 254(5030):432-7 (1991)). In fact, the nAChR-5HT3 chimera of the invention, containing the nAChR subunit sequences from N-terminal extracellular domain to the M2 domain, generate chimera receptors possessing at least some of the pharmacological characteristics of the given nAChR subunit. Further, chimeras containing only the 5HT3 sequence region within the large cytoplasmic loop located between the M3 and M4 preserve all the conserved transmembrane domains of nAChR subunits and appear to preserve most pharmacological characteristics of the native subunits.

The chimeras of the invention allow basic evaluation of the functional roles of the cytoplasmic loop. It has been noted that the chimeras exhibit differences in "acute desensitization," which makes reference to the rate with which the magnitude of the inward current flowing into the cell decreases during agonist application. Use of such chimeras in particular assay protocols presents certain advantages, e.g. for comparative purposes.

In certain embodiments, eukaryotic cells with nAChRs having chimeric subunits according to the invention are produced by introducing into the cell a first composition, which contains at least one RNA transcript that is translated in the cell into a subunit according to the invention. The subunits that can be translated include an α subunit of a human neuronal nicotinic AChR. The composition that is introduced can contain an RNA transcript which encodes an α subunit and also contains an RNA transcript which encodes a β subunit of a human neuronal nicotinic AChR. RNA transcripts can be obtained from cells transfected with DNAs encoding receptor subunits or by in vitro transcription of subunit-encoding DNAs. Methods for in vitro transcription of cloned DNA and injection of the resulting mRNA into eukaryotic cells are well known in the art. Amphibian oocytes are particularly preferred for expression of in vitro transcripts of the nAChR subunits provided herein. See, for example, Dascal, *CRC Crit. Rev. Biochem.* 22:317-387 (1989), for a review of the use of *Xenopus* oocytes to study ion channels.

Thus, pairwise (or stepwise) introduction of DNA or RNA encoding α and β subtypes into cells is possible. The resulting cells can be tested by the methods provided herein or known to those of skill in the art to detect functional AChR activity. Such testing will allow the identification of pairs of α and β subunit subtypes that produce functional AChRs, as well as individual subunits that produce functional AChRs.

As used herein, activity of a nicotinic AChR refers to any activity characteristic of an nAChR. Such activity can typically be measured by one or more in vitro methods, and frequently corresponds to an in vivo activity of a nicotinic AChR. Such activity can be measured by any method known to those of skill in the art, such as, for example, measuring the amount of current which flows through the recombinant channel in response to a stimulus.

Methods to determine the presence and/or activity of nicotinic AChRs include assays that measure nicotine binding, $^{86}$Rb ion-flux, $Ca^{2+}$ influx, the electrophysiological response of cells, the electrophysiological response of oocytes transfected with RNA from the cells, and the like. In particular, methods are provided herein for the measurement or detection of an AChR-mediated response upon contact of cells containing the DNA or mRNA with a test compound.

As used herein, a functional nicotinic AChR is a receptor that exhibits an activity of nicotinic AChRs as assessed by any in vitro or in vivo assay disclosed herein or known to those of skill in the art. Possession of any such activity that can be assessed by any method known to those of skill in the art and provided herein is sufficient to designate a receptor as functional. Because all combinations of α and β subunits may not form functional receptors, numerous combinations of α and β subunits can be tested in order to fully characterize a particular subunit and cells which produce same. Thus, as used herein, "functional" with respect to a recombinant or heterologous nicotinic AChR means that the receptor channel is able to provide for and regulate entry of nicotinic AChR-permeable ions, such as, for example, $Na^+$, $K^+$, $Ca^{2+}$ or $Ba^{2+}$, in response to a stimulus and/or bind ligands with affinity for the receptor. Preferably such nicotinic AChR activity is distinguishable, such as by electrophysiological, pharmacological and other means known to those of skill in the art, from any endogenous nicotinic AChR activity that may be produced by the host cell.

In accordance with a particular embodiment of the present invention, chimeric nicotinic AChR subunit-expressing mammalian cells or oocytes can be contacted with a test compound, and the modulating effect(s) thereof can then be evaluated by comparing the AChR-mediated response in the presence and absence of test compound, or by comparing the AChR-mediated response of test cells, or control cells (i.e., cells that do not express nAChRs), to the presence of the compound. Of course, effects of test compounds can be evaluated competitively in comparison to compounds known to modulate the receptors comprising the relevant subunits. Test compounds can also be evaluate based on their differential effect on receptors that comprise differing chimeric nAChR subunits.

As used herein, a compound or signal that "modulates the activity of a nicotinic AChR" refers to a compound or signal that alters the activity of nAChR so that activity of the nAChR is different in the presence of the compound or signal than in the absence of the compound or signal. In particular, such compounds or signals include agonists, antagonists, and partial agonists. The term agonist refers to a substance or signal, such as ACh, that activates receptor function; and the term antagonist refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

An "agonist" can be a substance that activates its binding partner. Activation can be defined in the context of the particular assay, or may be apparent in the literature from a discussion herein that makes a comparison to a factor or substance that is accepted as an "agonist" or "partial agonist" of the particular binding partner by those of skill in the art. Activation can be defined with respect to an increase in a particular effect or function that is induced by interaction of the agonist or partial agonist with a binding partner and can include allosteric effects. An "antagonist" can be a substance that inhibits its binding partner, typically a receptor. Inhibition is defined in the context of the particular assay, or can be apparent in the literature from a discussion herein that makes a comparison to a factor or substance that is accepted as an "antagonist" of the particular binding partner by those of skill in the art. Inhibition can be defined with respect to a decrease in a particular effect or function that is induced by interaction of the agonist with a binding partner, and can include allosteric effects.

As understood by those of skill in the art, assay methods for identifying compounds that modulate nicotinic AChR activity (e.g., agonists, antagonists, and partial agonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture can be a cell or a culture of cells which are identical to the transfected cells, except the cells employed for the control culture do not express functional nicotinic AChRs. In this situation, the response of test cell to test compound is compared to the response (or lack of response) of receptor-negative (control) cell to test compound, when cells or cultures of each type of cell are exposed to substantially the same reaction conditions in the presence of compound being assayed.

As used herein, a human "α subunit" gene is a gene that encodes an α subunit of a human neuronal nicotinic acetylcholine receptor. The α subunit is a subunit of the nAChR to which ACh binds. Assignment of the name "α" to a putative nAChR subunit, according to Deneris et al., *TIPS* 12:34-40 (1991), is based on the conservation of adjacent cysteine residues in the presumed extracellular domain of the subunit that are the homologues of cysteines 192 and 193 of the Torpedo α subunit (see Noda et al. *Nature* 299:793-797 (1982)). An α subunit also binds to ACh under physiological conditions and at physiological concentrations and, in the optional presence of a β subunit (i.e., some α subunits are functional alone, while others require the presence of a β subunit), generally forms a functional AChR as assessed by methods described herein or known to those of skill in this art.

Also contemplated are α subunits encoded by DNAs that encode α subunits as defined above, but that by virtue of degeneracy of the genetic code do not necessarily hybridize to the disclosed DNA under specified hybridization conditions. Such subunits also form a functional receptor, as assessed by the methods described herein or known to those of skill in the art, generally with one or more β subunit subtypes.

As used herein, a human "β subunit" gene is a gene that encodes a β subunit of a human neuronal nicotinic acetylcholine receptor. Assignment of the name "β" to a putative nAChR subunit, according to Deneris et al. supra, is based on the lack of adjacent cysteine residues (which are characteristic of α subunits). The β subunit is frequently referred to as the structural nAChR subunit (although it is possible that β subunits also have ACh binding properties). Combination of β subunit(s) with appropriate α subunit(s) leads to the formation of a functional receptor (for those α subunits that require a β subunit).

Also contemplated are β subunits encoded by DNAs that encode β subunits as defined above, but that by virtue of degeneracy of the genetic code do not necessarily hybridize to the disclosed DNA or deposited clones under the specified hybridization conditions. Such subunits also form functional receptors, as assessed by the methods described herein or known to those of skill in the art, in combination with appropriate α subunit subtype(s).

Nucleic Acid Molecules

As is known in the art for any DNA sequence determined by an automated approach, any nucleotide sequence disclosed herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequences in FIGS. 2, 4, and 6 (SEQ ID NOS: 6, 8, and 10, respectively), a nucleic acid molecule of the present invention encoding an chimeric nAChR subunit polypeptide can be obtained using standard cloning and screening procedures, such as those for cloning cDNAs using mRNA as starting material.

As indicated, nucleic acid molecules of the present invention can be in the form of RNA, such as mRNA, or in the form of DNA, including, for instance, cDNA and genomic DNA obtained by cloning or produced synthetically. The DNA can be double-stranded or single-stranded. Single-stranded DNA or RNA can be the coding strand, also known as the sense strand, or it can be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIGS. 2, 4, and 6 (SEQ ID NOS: 6, 8, and 10, respectively); DNA molecules comprising the coding sequence for the chimeric nAChR subunit protein shown in FIGS. 3, 5, and 7 (SEQ ID NOS: 7, 9, and 11, respectively); and DNA molecules which comprise a sequence substantially different from those described above but which, due to the degeneracy of the genetic code, still encode the chimeric nAChR subunit protein. Of course, the genetic code is well known in the art. Thus, it would be routine for one skilled in the art to generate such degenerate variants. The present invention also includes other nucleic acid molecules and polypeptides defined according to the structural and functional requirements as disclosed herein.

Nucleic acids encoding portions of the chimeric nAChR subunit include nucleic acids determined by hybridization to those nucleic acids disclosed herein. Accordingly, the invention provides an isolated nucleic acid molecule comprising a polynucleotide which hybridizes under stringent hybridization conditions to a portion of the polynucleotide in a nucleic acid molecule of the invention described above, for instance, the polynucleotides disclosed in FIGS. 2, 4, and 6 (SEQ ID NOS: 6, 8, and 10, respectively). By "stringent hybridization conditions" is intended overnight incubation at 42° C. in a solution comprising: 50% formamide, 5× SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1× SSC at about 65° C.

As indicated, nucleic acid molecules of the present invention that encode an chimeric nAChR subunit polypeptide can include, but are not limited to, those encoding the amino acid sequence of the polypeptide, by itself; the coding sequence for the polypeptide and additional sequences, such as those encoding a leader or secretory sequence, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example-ribosome binding and stability of mRNA; an additional coding sequence which codes for additional amino acids, such as those which provide additional functionalities. Thus, the sequence encoding the polypeptide can be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the chimeric nAChR subunit fused to Fc at the N- or C-terminus. The FLAG peptide (Asp-TyrLysAspAspAspAspLys) (Sigma Chemical Company, St Louis, Mo.), commonly used for the isolation, purification, and detection of recombinant proteins expressed in *E. coli*, has been used in particular examples of the present invention, e.g. the chimeric α4 receptor as disclosed herein.

The present invention further relates to variants of the nucleic acid molecules of the present invention, which encode portions, analogs or derivatives of the chimeric nAChR subunit protein. Variants can occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants can be produced using art-known mutagenesis techniques.

Such variants include those produced by nucleotide substitutions, deletions or additions which can involve one or more nucleotides. The variants can be altered in coding regions, non-coding regions, or both. Alterations in the coding regions can produce conservative or non-conservative amino acid substitutions, deletions or additions. Especially preferred among these are silent substitutions, additions and deletions, which do not alter the properties and activities of the chimeric nAChR subunit protein or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the chimeric nAChR subunit polypeptide having the complete amino acid sequence in FIG. 3, 5, or 7 (SEQ ID NOS: 7, 9, or 11, respectively) or any other sequence according to the present invention; (b) a nucleotide sequence encoding the chimeric nAChR subunit polypeptide having the amino acid sequence in FIGS. 1A and B (SEQ ID NO:2), but lacking the N-terminal methionine; (c) a nucleotide sequence encoding a portion of the chimeric nAChR subunit polypeptide from a source sequence in accordance with the disclosed structure of the chimeric subunit, i.e. a nucleotide sequence meeting the above criteria relative to the native nAChR subunit component or the substituted portion based on comparison to the sequence of the native source sequence; and (h) a nucleotide sequence complementary to any of the nucleotide sequences in (a), (b), (c), (d), (e), (f) or (g) above.

By a polynucleotide having a nucleotide sequence at least, for example, 95% "identical" to a reference nucleotide sequence encoding an chimeric nAChR subunit polypeptide is intended that the nucleotide sequence of the polynucleotide is identical to the reference sequence except that the polynucleotide sequence can include up to five point mutations per each 100 nucleotides of the reference nucleotide sequence encoding the chimeric nAChR subunit polypeptide. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence of SEQ ID NOS: 6, 8, or 10, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence can include up to five point mutations per each 100 nucleotides of the reference nucleotide sequence encoding the chimeric nAChR subunit polypeptide. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. The query sequence can be an entire sequence shown in FIG. 2, 4, or 6 (SEQ ID NOS: 6, 8, or 10, respectively), the ORF (open reading frame), or any fragment specified as described herein, e.g. domains of the native nAChR or the portion substituted to form the chimera.

As a practical matter, whether any particular nucleic acid molecule or polynucleotide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a match/alignment of the first 10 bases at the 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the nucleic acid sequence shown in FIGS. 2, 4, and 6 (SEQ ID NOS: 6, 8, or 10, respectively) will encode a polypeptide "having chimeric nAChR subunit protein activity." In fact, because degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having chimeric nAChR subunit protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," Science 247:1306-1310 (1990), wherein the authors indicate that proteins are surprisingly tolerant of amino acid substitutions.

Chimeric nAChR Subunit Polypeptides

It will be recognized in the art that some amino acid sequences of the chimeric nAChR subunit polypeptide can be varied without significant effect of the structure or function of the protein. If such differences in sequence are contemplated, it should be remembered that there will be critical areas on the protein which determine activity.

The examples of the polypeptides of the present invention, for example those shown in FIGS. 3, 5, and 7 (SEQ ID NOS: 7, 9, or 11, respectively), comprise an insertion derived from mouse serotonin type 3 receptors (m5HT3R). The illustrative insert is taken from the region of the mouse receptor that is considered somewhat structurally analogous to the corresponding region of the native nAChR receptor subunit that is being replaced.

In addition to the m5HT3 cytoplasmic +/−M3/M4 sequences used to produce a chimeric receptor according to the examples of the invention, e.g. as shown in the Figures, corresponding sequences can be switched between nicotinic receptor subunits. For example, internal sequences from subunits that assemble as homopentamers can be used as substituted sequences, e.g. internal sequences from the $\alpha 7$ subunit. Like the 5HT3 subunits, $\alpha 7$ subunits assemble well as homopentamers, indicating that their external and internal sequences are all compatible with such assembly. Further, the mouse 5HT3 subunit sequence from the "B" variant can also be used (the sequence disclosed in the figures herein is from the "A" variant) (Hanna, M. C., et al., Evidence for expression of heteromeric serotonin 5-HT(3) receptors in rodents. *J. Neurochem.* 75 (1):240-247 (2000)). In fact, any cytoplasmic +/−M3/M4 sequences from any member of the 4-transmembrane domain family of subunits including from GABA-A or glycine receptors as well as 5HT3 and nAChR subunits can be used (Buckle, V. J. et al., Chromosomal localization of GABAA receptor subunit genes: relationship to human genetic disease. Neuron 3 (5):647-654 (1989); Pierce, K. D., et al., A nonsense mutation in the $\alpha 1$ subunit of the inhibitory glycine receptor associated with bovine myoclonus. *Mol. Cell. Neurosci.* 17 (2):354-363 (2001)).

It will further be appreciated that, depending on the criteria used, concerning the exact "address" of the extracellular, intracellular and transmembrane domains of the chimeric nAChR subunit polypeptide differ slightly. For example, the exact location of the chimeric nAChR subunit extracellular domains illustrated schematically in FIG. 9 can vary slightly (e.g., the address can "shift" by about 1 to 5 residues) depending on the criteria used to define the domain.

Thus, the invention further includes variations of the chimeric nAChR subunit polypeptide which show substantial chimeric nAChR subunit polypeptide activity or which include regions of chimeric nAChR subunit protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, the fragment, derivative or analog of the polypeptide of FIG. 3, 5, or 7 (SEQ ID NOS: 7, 9, or 11, respectively) or any other sequence according to the present invention, can be (i) one in which one or more of the amino acid residues (e.g., 3, 5, 8, 10, 15 or 20) are substituted with a conserved or non-conserved amino acid residue (preferably a conserved amino acid residue) and such substituted amino acid residue may or may not be one encoded by the genetic code, or (ii) one in which one or more of the amino acid residues includes a substituent group (e.g., 3, 5, 8, 10, 15 or 20), or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the chimeric nAChR subunit protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-α to only one of the two known types of TNF receptors. Thus, the chimeric nAChR subunit receptor of the present invention can include one or more (e.g., 3, 5, 8, 10, 15 or 20) amino acid substitutions, deletions or additions, either from natural mutations or human manipulation.

As indicated, changes are preferably of a minor nature, such as conservative amino acid substitutions that do not significantly affect the folding or activity of the protein (see below):

| Conservative Amino Acid Substitutions | |
| --- | --- |
| Aromatic: | Phenylalanine, Tryptophan, Tyrosine |
| Hydrophobic: | Leucine, Isoleucine, Valine |
| Polar: | Glutamine, Asparagine |
| Polar Hydroxyl: | Serine, Threonine |
| Basic: | Arginine, Lysine, Histidine |
| Acidic: | Aspartic Acid, Glutamic Acid |
| Small: | Alanine, Serine, Threonine, Methionine, Glycine |

Of course, the number of amino acid substitutions a skilled artisan would make depends on many factors, including those described above. Generally speaking, the number of substitutions for any given chimeric subunit polypeptide will not be more than 50, 40, 30, 25, 20, 15, 10, 5 or 3.

Amino acids in the chimeric nAChR subunit protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:399-904 (1992) and de Vos et al. *Science* 255:306-312 (1992)).

Even if deletion of one or more amino acids from the N-terminus of a protein results in modification or loss of one or more biological functions of the protein, other biological activities can still be retained. Thus, the ability of shortened chimeric nAChR subunit muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a chimeric nAChR subunit mutein with a large number of deleted N-terminal amino acid residues can retain some biological or immunogenic activities. In fact, peptides composed of as few as six chimeric nAChR subunit amino acid residues can often evoke an immune response.

As mentioned above, even if deletion of one or more amino acids from the C-terminus of a protein results in modification or loss of one or more biological functions of the protein, other biological activities can still be retained. Thus, the ability of the shortened chimeric nAChR subunit mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a chimeric nAChR subunit mutein with a large number of deleted C-terminal amino acid residues can retain some biological or immunogenic activities. In fact, peptides composed of as few as six chimeric nAChR subunit amino acid residues can often evoke an immune response.

Accordingly, the present invention further provides polypeptides having one or more residues deleted from the carboxy terminus of the amino acid sequence of the chimeric nAChR subunit polypeptide shown in FIG. 3, 5, or 7 (SEQ ID NOS: 7, 9, or 11, respectively) or any other sequence according to the present invention, and polynucleotides encoding such polypeptides. The invention also provides polypeptides having one or more amino acids deleted from both the amino and the carboxyl termini of a chimeric nAChR subunit polypeptide. It is also contemplated that polypeptides useful in production of the "isolated polypeptides" of the invention can produced by solid phase synthetic methods. See Houghten, R. A., *Proc. Natl. Acad. Sci. USA* 82:5131-5135 (1985); and U.S. Pat. No. 4,631,211 to Houghten et al. (1986).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host. For example, a recombinantly produced version of the chimeric nAChR subunit polypeptide can be substantially purified by the one-step method described in Smith and Johnson, *Gene* 67:31-40 (1988).

By a polypeptide having an amino acid sequence at least, for example, 95% "identical" to a reference amino acid sequence of an chimeric nAChR subunit polypeptide is intended that the amino acid sequence of the polypeptide is identical to the reference sequence except that the polypeptide sequence can include up to five amino acid alterations per each 100 amino acids of the reference amino acid of the chimeric nAChR subunit polypeptide. In other words, to obtain a polypeptide having an amino acid sequence at least 95% identical to a reference amino acid sequence, up to 5% of the amino acid residues in the reference sequence can be deleted or substituted with another amino acid, or a number of amino acids up to 5% of the total amino acid residues in the reference sequence can be inserted into the reference sequence. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 3, 5, or 7 (SEQ ID NOS: 7, 9, or 11, respectively) or any other sequence according to the present invention, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in FIG. 3, 5, or 7 (SEQ ID NOS: 7, 9, or 11, respectively) or any other sequence according to the present invention, can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. *Comp. App. Biosci.* 6:237-245 (1990). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty-1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues of the query (reference) sequence that extend past the N- or C-termini of the subject sequence are considered for the purposes of manually adjusting the percent identity score. That is, only residues which are not matched/aligned with the N- or C-termini of the query sequence are counted when manually adjusting the percent identity score.

For example, a 90 amino acid residue subject sequence is aligned with a 100 residue query sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

The invention encompasses chimeric nAChR subunit polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. The polypeptides can also be modified with a detectable label, such as an enzymatic, fluorescent, isotopic or affinity label to allow for detection and isolation of the protein.

Preparation of Chimeric Gene Fusions

Generally speaking, the chimera gene fusions can be engineered using several steps of Polymerase Chain Reaction (PCR). Stepwise details of genetic engineering for two types of chimera cDNA construction are illustrated and described in FIG. 11. In order to produce one kind of chimera having the general structure illustrated in FIG. 11(I), the experimental design illustrated in (I) is used to construct two discontinuous fragments, A and B. Then, the PCR operation is applied again but using different primer sets to fuse relevant protions of the A and B fragments into a continuous strand of cDNA having the ability to code for the desired chimeric subunit.

Figure 11:
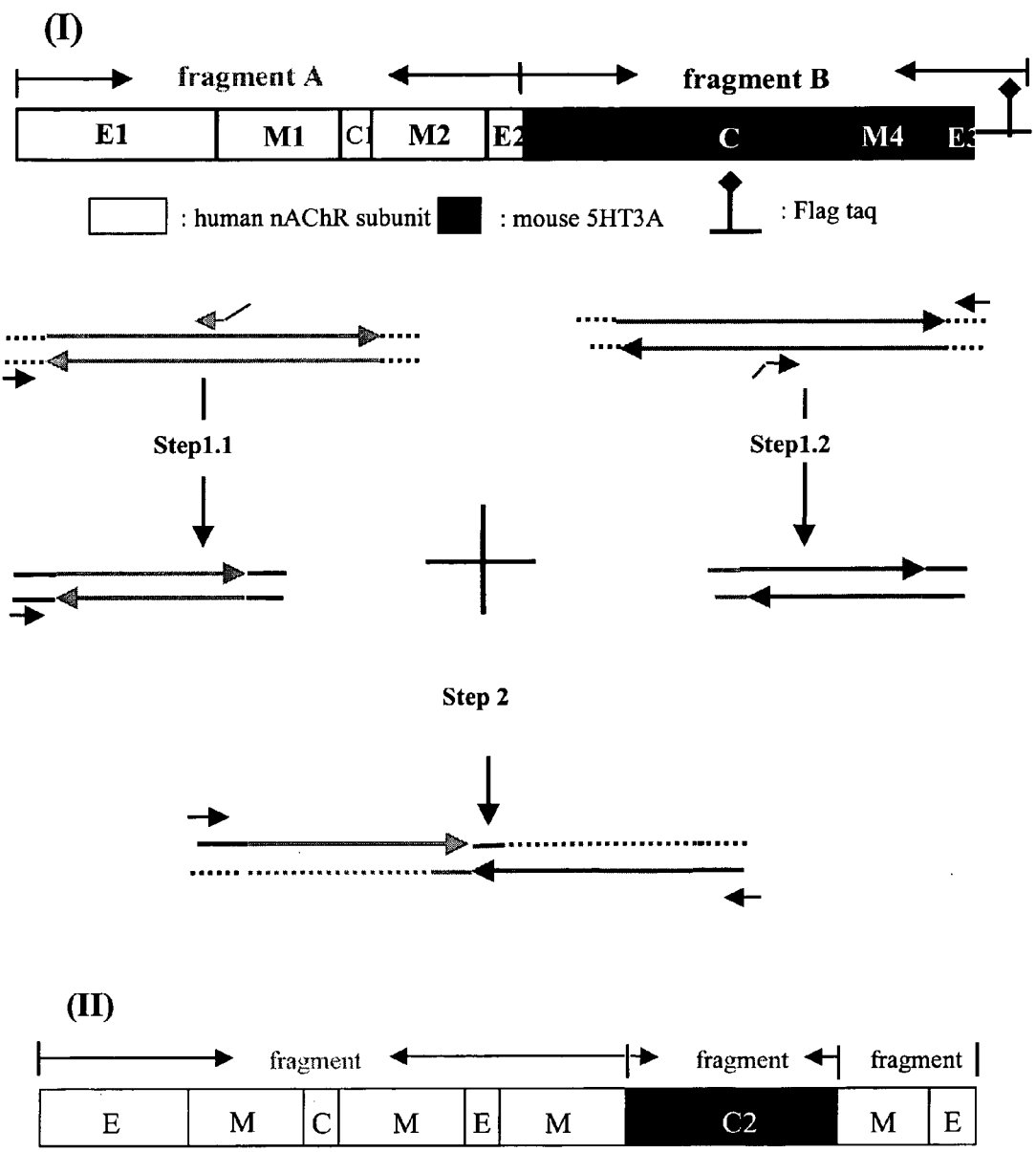
FIG. 11 is a schematic representation of one embodiment of the method used for production of the chimeric polynucleotides of the invention. (I) Step 1.1: PCR amplification of fragment A using nAChR subunit gene cDNA template, vector sense primer, and a custom-designed antisense primer with 5' m5HT3 and 3' nAChR subunit sequence spanning the projected fusion junction. Step 1.2: PCR amplification of fragment B using mSHT3 gene cDNA template, vector antisense primer, and a custom-designed sense primer with 5' nAChR subunit and 3' m5HT3 sequence spanning the projected fusion junction. Step 2: Mixing of PCR product from step 1.1 & 1.2, heating to denature DNA duplex, allowing single-stranded fragments A and B to anneal, extending the novel partial duplex DNA with DNA polymerase, followed by PCR using vector sense and antisense primers to amplify desired fragments. (II) is a schematic representation of the chimeric polynucleotide obtained by the steps outlined in (I).

In order to produce another kind of chimera having the general structure illustrated in FIG. 11(II), the experimental design modified to construct three discontinuous fragments, A, B and C. Then, the PCR operation is applied again but using different primer sets to fuse relevant protions of the A and B fragments. Another round of the PCR operation is than conducted using another set of primers to fuse the A+B to the C fragment to produce a continuous strand of cDNA having the ability to code for the desired chimeric subunit.

The resulting chimeric cDNAs are then digested with restriction enzymes to confirm their structure and sequence and processed in a separate operation so that they can be cloned into an appropriate expression vector before being delivered into a host cell line, e.g. SH-EPI. In one embodiment, the fusion gene is inserted to the pcDNA3.1/hyg (Invitrogen Corporation, Carlsbad, Calif.) for α4 or pcDNA3.1/zeo (Invitrogen Corporation, Carlsbad, Calif.) for β2 and β4 cloning/mammalian expression vectors as Hind III-Xba I or EcoR I-XbaI fragment, respectively. The pcDNA expression vectors use the CMV promoter. Other useful expression systems are the pEF series having a hEF-1α promoter (such as pEF6/Myc-His) (Invitrogen Corporation, Carlsbad, Calif.). The pCEP4 episomal vector can also be used (Invitrogen Corporation, Carlsbad, Calif.). Additional information regarding vectors from Invitrogen Corporation is available at http://www.invitrogen.com. (also, see below regarding Vectors and Host Cells).

Vectors and Host Cells

The present invention also relates to vectors which include the isolated DNA molecules of the present invention, host cells which are genetically engineered with the recombinant vectors, and the production of chimeric nAChR subunit polypeptides or fragments thereof by recombinant techniques.

The polynucleotides can be joined to a vector containing a selectable marker for propagation in a host by using techniques that are known to those familiar in the art, and that generally involve restriction enzyme cleavage of the circular vector at a specific site in such a way that the polynucleotide of interest, sometimes also treated with restriction enzyme to optimally prepare it for the joining process, will anneal to the linearized vector via blunt-end or complementary end ligation. Typically, the unligated products are then separated from the ligated product of interest containing the polynucleotide of interest contained within the vector, and the isolated vector-polynucleotide complexes are cloned through a process involving transformation of bacteria prior to subsequent analysis to confirm presence of the polynucleotide and that it is in the correct orientation for subsequent expression. If the vector is a virus, it can be packaged in vitro using an appropriate packaging cell line so that the virus contains the polynucleotide of interest in the appropriate form and structure.

The DNA insert can be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Examples of mammalian expression vectors useful according to the present invention also include pTRE for regulated control of gene expression, e.g. pTRE HA (with HA epitope) BD Biosciences Clontech, Palo Alto, Calif. (for additional information see http://www.clontech.com/techinfo/vectors/vectorsT-Z/pTRE-HA.shtml). Cell line variants, e.g. large T-antigen-expressing HEK cells, allow high expression from the SV40 promoter in mammalian cells), and the 3'-poly-A signal can be tailored to optimize expression and translation efficiency.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The vectors used for prokaryotic expression also contain a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986). If the vector is a virus, it can be packaged in vitro using an appropriate packaging cell line and then transduced into host cells.

The polypeptide can be expressed in a modified form, such as a fusion protein, and can include not only secretion signals, but also additional heterologous functional regions. For instance, a region of additional amino acids, particularly charged amino acids, can be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hiL-5. See Bennett, D., et al., *J. Mol. Recog.*, 8:52-58 (1995) and Johanson, K. et al., *J. Biol. Chem.*, 270(16):9459-9471 (1995).

The chimeric nAChR subunit protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention can be glycosylated or can be non-glycosylated. In addition, polypeptides of the invention can also include an initial modified methionine residue, in some cases as a result of host-mediated processes.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., chimeric nAChR subunit coding sequence), and/or to include genetic material (e.g., heterologous polynucleotide sequences) that is operably associated with chimeric nAChR subunit polynucleotides of the invention, and which activates, alters, and/or amplifies endogenous chimeric nAChR subunit polynucleotides. For example, techniques known in the art can be used to operably associate heterologous control regions (e.g., promoter and/or enhancer) and endogenous chimeric nAChR subunit polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932-8935 (1989); and Zijlstra et al., *Nature* 342:435-438 (1989), the disclosures of each of which are incorporated by reference in their entireties).

Appropriate cells include SH-EP type cells (e.g. SH-EP1), HEK-293 (human embryonic kidney), IMR-32 human neuroblastoma cells, and CATH.a mouse neuronal cells. (See Lukas, R. J., et al., "Some Methods of Studies of Nicotinic Acetylcholine Receptor Pharmacology," Ch. 1, in Methods & New Frontiers in Neuroscience, CRC Press LLC (2002), and citations therein). SH-EP type cells can be obtained from the human neuroblastoma parental cell line SK-N-SH (See Ross, R. A., et al., "Coordinate Morphological and Biochemical Interconversion of Human Neuroblastoma Cells," *JNCI*, 71(4):741-749 (1983)). SH-EP ("EP" for epithelial-like morphology) cells are morphologically distinguishable, lack expression of noradrenergic enzyme activity (tyrosine hydroxylase and dopamine-β-hydroxylase), and contain an isochromosome 1q (long arm of chromosome 1) (Ross, et al., 1983). Without wishing to be bound by any particular theory, it appears that such cells can be useful because they possess and properly express complex transmembrane proteins due to their neuroepithelial lineage, while having lost expression of native nAChRs which could otherwise complicate analysis involving heterologous expression of nAChRs. (See Lukas, R. J. et al., 2002).

Those of skill in the art will recognize that the suitability of particular cell lines for heterologous expression of nAChRs according to the invention can be determined empirically, and that the foregoing guidance will provide direction for development of useful models beyond the examples expressly provided herein.

Transgenic Non-Human Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees can be used to generate transgenic animals. In a specific embodiment, techniques described herein or otherwise known in the art, are used to express polypeptides of the invention in humans, as part of a gene therapy protocol.

Any technique known in the art can be used to introduce the transgene (i.e., polynucleotides of the invention) into animals to produce the founder lines of transgenic animals. Such techniques include, but are not limited to, pronuclear microinjection (Paterson et al., *Appl. Microbiol. Biotechnol.* 40:691-698 (1994); Carver et al., *Biotechnology (NY)* 11:1263-1270 (1993); Wright et al., *Biotechnology (NY)* 9:830-834(1991); and Hoppe et al., U.S. Pat. No. 4,873,191 (1989)); retrovirus mediated gene transfer into germ lines (Van der Putten et al., *Proc. Natl. Acad. Sci., USA* 82:6148-6152 (1985)), blastocysts or embryos; gene targeting in embryonic stem cells (Thompson et al., *Cell* 56:313-321 (1989)); electroporation of cells or embryos (Lo, *Mol Cell. Biol.* 3:1803-1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717-723 (1989); etc. For a review of such techniques, see Gordon, "Transgenic Animals," *Intl. Rev. Cytol.* 115:171-229 (1989), which is incorporated by reference herein in its entirety. Further, the contents of each of the documents recited in this paragraph are herein incorporated by reference in their entirety.

Any technique known in the art can be used to produce transgenic clones containing polynucleotides of the invention, for example, nuclear transfer into enucleated oocytes of nuclei from cultured embryonic, fetal, or adult cells induced to quiescence (Campell et al., *Nature* 380:64-66 (1996); Wilmut et al., *Nature* 385:810-813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric. The transgene can be integrated as a single transgene or as multiple copies such as in concatamers, e.g., head-to-head tandems or head-to-tail tandems. The transgene can also be selectively introduced into and activated in a particular cell type by following, for example, the teaching of Lasko et al., *Proc. Natl. Acad. Sci. USA* 89:6232-6236 (1992). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene can also be selectively introduced into a particular cell type, thus inactivating the endogenous gene in only that cell type, by following, for example, the teaching of Gu et al., *Science* 265:103-106 (1994). The regulatory sequences required for such a cell-type specific inactivation will depend upon the particular cell type of interest, and will be apparent to those of skill in the art. The contents of each of the documents recited in this paragraph are herein incorporated by reference in their entirety.

Once transgenic animals have been generated, the expression of the recombinant gene can be assayed utilizing standard techniques. Initial screening can be accomplished by Southern blot analysis or PCR techniques to analyze animal tissues to verify that integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue can also be evaluated immunocytochemically or immunohistochemically using antibodies specific for the transgene product.

Once the founder animals are produced, they can be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Having generally described the invention, the same will be more readily understood by reference to the following examples, which are provided by way of illustration only.

EXAMPLES

Example 1

Expression of Chimeric nAChR Subunits in Oocytes

*Xenopus* oocytes are injected with in vitro transcripts prepared from constructs containing DNA encoding chimeric $\alpha 4$, $\beta 2$, and $\beta 4$ subunits. Electrophysiological measurements of the oocyte transmembrane currents are made using the two-electrode voltage clamp technique (see, e.g., Stuhmer, *Meth. Enzymol.* 207:319-339 (1992)).

1. Preparation of in vitro Transcripts

Recombinant capped transcripts of pCMV expression constructs are synthesized from linearized plasmids using the mCAP RNA Capping Kit (Cat. #200350 from Stratagene, Inc., La Jolla, Calif.). The mass of each synthesized transcript is determined by UV absorbance and the integrity of each transcript was determined by electrophoresis through an agarose gel.

2. Electrophysiology

*Xenopus* oocytes are injected with either 12.5, 50 or 125 ng of chimeric nAChR subunit transcript per oocyte. The preparation and injection of oocytes is carried out as described by Dascal in *Crit. Rev. Biochem.* 22:317-387 (1987). Two-to-six days following mRNA injection, the oocytes are examined using the two-electrode voltage clamp technique. The cells are bathed in Ringer's solution (115 mM NaCl, 2.5 mM KCl, 1.8 mM $CaCl_2$, 10 mM HEPES, pH 7.3) containing 1 μM atropine with or without 100 μM d-tubocurarine. Cells are voltage-clamped at −60 to −80 mV. Data are acquired with axotape software at 2-5 Hz. The agonists acetylcholine (ACh), nicotine, and cytisine are added at concentrations ranging from 0.1 μM to 100 μM.

The current response of injected oocytes to 10 μM ACh is also examined in terms of membrane voltage. In these experiments, voltage steps are applied to the cells in the presence of ACh. The contribution of $Ca^{++}$ flux to the total current can be ascertained by varying the calcium concentration in the external medium and taking multiple current measurements at different holding potentials around the reversal potential. Such studies indicate whether the channel carrying the current generated in response to ACh treatment of injected oocytes is permeable to $Na^+$, $K^+$ and $Ca^{++}$.

Example 2

Recombinant Expression of chimeric nAChR Subunits in Mammalian Cells

Human embryonic kidney (HEK) 293 cells are transiently and stably transfected with DNA encoding chimeric nAChR subunits. Transient transfectants were analyzed for expression of nicotinic AChR using various assays, e.g., electrophysiological methods, $Ca^{++}$-sensitive fluorescent indicator-based assays, and [$^{125}$I]-α-bungarotoxin-binding assays.

1. Transient Transfection of HEK Cells

About $2 \times 10^6$ HEK cells are transiently transfected with 18 μg of the plasmid(s) bearing the chimeric subunit expression constructs according to standard $CaPO_4$ transfection procedures (Wigler et al., *Proc. Natl. Acad. Sci. USA* 76:1373-1376 (1979)). In addition, 2 μg of plasmid pCMV βgal (Clontech Laboratories, Palo Alto, Calif.), which contains the *Escherichia coli*, β-galactosidase gene fused to the CMV promoter, are co-transfected as a reporter gene for monitoring the efficiency of transfection. The transfectants are analyzed for β-galactosidase expression by measurement of β-galactosidase activity (Miller, Experiments in Molecular Genetics, pp. 352-355, Cold Spring Harbor Press (1972)). Transfectants can also be analyzed for β-galactosidase expression by direct staining of the product of a reaction involving β-galactosidase and the X-gal substrate (Jones, *EMBO* 5:3133-3142(1986)).

2. Stable Transfection of HEK Cells

HEK cells are transfected using the calcium phosphate transfection procedure (Current Protocols in Molecular Biology, Vol. 1, Wiley Inter-Science, Supplement 14, Unit 9.1.1-9.1.9 (1990)). Ten-cm plates, each containing one-to-two million HEK cells are transfected with 1 ml of DNA/calcium phosphate precipitate containing 9.5 μg of each pCMV chimeric subunit expression construct and 1 μg pSV2neo (as a selectable marker). After 14 days of growth in media containing 1 μg/ml G418, colonies form and are individually isolated by using cloning cylinders. The isolates are subjected to limiting dilution and screened to identify those that expressed the highest level of nicotinic AChR, as described below.

3. Analysis of Transfectants a. Fluorescent Indicator-Based Assays

Activation of the ligand-gated nicotinic AChR by agonists leads to an influx of cations, including $Ca^{++}$, through the receptor channel. $Ca^{++}$ entry into the cell through the channel can induce release of calcium contained in intracellular stores. As one example, a receptor comprising a chimeric nAChR subunit of the invention (comprising chimeric subunits of α4 and β2) exhibited a two-fold increase in net current compared to the wild-type counterpart when exposed to a compound known to specifically activate α4β2 nAChR.

Monovalent cation entry into the cell through the channel can also result in an increase in cytoplasmic $Ca^{++}$ levels through depolarization of the membrane and subsequent activation of voltage-dependent calcium channels. Therefore, methods of detecting transient increases in intracellular calcium concentration can be applied to the analysis of functional nicotinic AChR expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.), are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{++}$ concentration of cells containing the indicator can be expressed directly as an increase in fluorescence. An automated fluorescence detection system for assaying nicotinic AChR has been described in PCT Patent Application No. PCT/US92/11090.

HEK cells that have been transiently or stably co-transfected with DNA encoding chimeric subunits are analyzed for expression of functional recombinant nicotinic AChR using the automated fluorescent indicator-based assay. The assay procedure is as follows.

Untransfected HEK cells (or HEK cells transfected with expression vector alone) and HEK cells that have been co-transfected with expression constructs of the invention are plated in the wells of a 96-well microtiter dish and loaded with fluo-3 by incubation for 2 hours at 20° C. in a medium containing 20 μM fluo-3, 0.2% Pluronic F-127 in HBS (125 mM NaCl, 5 mM KCl, 1.8 mM $CaCl_2$, 0.62 mM $MgSO_4$, 6 mM glucose, 20 mM HEPES, pH 7.4). The cells are then washed with assay buffer (i.e., HBS). The antagonist d-tubocurarine is added to some of the wells at a final concentration of 10 μM. The microtiter dish is then placed into a fluorescence plate reader and the basal fluorescence of each well is measured and recorded before addition of 200 μM nicotine to the wells. The fluorescence of the wells is monitored repeatedly during a period of approximately 60 seconds following addition of nicotine.

The fluorescence of the untransfected HEK cells (or HEK cells transfected with vector along) should not change after addition of nicotine. In contrast, the fluorescence of the co-transfected cells, in the absence of d-tubocurarine, is expected to increase significantly after addition of nicotine to the wells. This nicotine-stimulated increase in fluorescence should not be observed in co-transfected cells exposed to the antagonist d-tubocurarine. These tests can demonstrate whether the co-transfected cells express functional recombinant AChR activated by nicotine and blocked by d-tubocurarine.

b. α-Bungarotoxin Binding Assays

HEK293 cells transiently transfected with pCMV expression constructs according to the invention are analyzed for [$^{125}$I]-α-bungarotoxin (BgTx) binding. Whole transfected cells and membranes prepared from transfected cells are examined in these assays. Rat brain membranes are included in the assays as a positive control.

Rat brain membranes are prepared according to the method of Hampson et al., *J. Neurochem* 49:1209 (1987). Membranes were prepared from the HEK cells transfected with pCMV expression constructs and HEK cells transiently transfected with plasmid pUC19 only (negative control) according to the method of Perez-Reyes et al., *Nature* 340:233 (1989). Whole transfected and negative control cells are obtained by spraying the tissue culture plates with phosphate-buffered saline containing 0.1% (w/v) BSA. The cells are then centrifuged at low speed, washed once, resuspended in assay buffer (118 mM NaCl, 4.8 mM KCl, 2.5 mM $CaCl_2$, 1.2 mM $MgSO_4$, 20 mM HEPES, 0.1% (w/v) BSA, 0.05% (w/v) bacitracin and 0.5 mM PMSF, pH 7.5) and counted.

Specific binding of [$^{125}$I]-α-BgTx to rat brain membranes is determined essentially as described by Marks et al., *Molec. Pharmacol.* 22:554-564(1982), with several modifications. The membranes are washed twice in assay buffer. The assay is carried out in 12×75 mm polypropylene test tubes in a total volume of 0.5 ml assay buffer. The membranes are incubated with 10 nM [$^{125}$I]-α-BgTx (New England Nuclear, Boston, Mass.) for one hour at 37° C. The assay mixtures are then centrifuged at 2300×g for 10 minutes at 4° C. The supernatant is decanted and the pellets are washed twice with 2 ml aliquots of ice-cold assay buffer. The supernatants are decanted again and the radioactivity of the pellets is measured in a γ-counter. Nonspecific binding is determined in the presence of 1 μM unlabeled α-BgTx. Specific binding is determined by subtracting nonspecific binding from total binding. Specific binding of [$^{125}$I]-α-BgTx to membranes prepared from transfected and negative control cells is determined as described for determining specific binding to rat brain membranes except that the assay buffer does not contain BSA, bacitracin and PMSF. Specific binding of [$^{125}$I]-α-BgTx to transfected and negative control whole cells is determined basically as described for determining specific binding to rat brain membranes.

[$^{125}$I]-α-BgTx binding is evaluated as a function of membrane concentration and as a function of incubation time. [$^{125}$I]-α-BgTx binding to rat brain membranes is expected to increase in a linear fashion with increasing amounts of membrane (ranging between 25-500 μg).

To monitor [$^{125}$I]-α-BgTx binding to rat brain membranes and whole transfected and negative control cells, 300 μg of membrane or 500,000 cells are incubated with 1 nM or 10 nM [$^{125}$I]-α-BgTx, respectively, at 37° C. for various times ranging from 0-350 min. Aliquots of assay mixture are transferred to 1.5 ml microfuge tubes at various times and centrifuged. The pellets are washed twice with assay buffer.

Example 3

Characterization of Cell Lines Expressing nAChRs

Recombinant cell lines generated by transfection with DNA encoding chimeric nAChR subunits of the invention can be further characterized using one or more of the following methods.

A. Northern or Slot Blot Analysis for Expression of α- and/or β-Subunit Encoding Messages Total RNA is isolated from about $1 \times 10^7$ cells and 10-15 μg of RNA from each cell type is used for northern or slot blot hybridization analysis. The inserts from chimeric nAChR-encoding plasmids can be nick-translated and used as probe. In addition, the β-actin gene sequence (Cleveland et al., *Cell* 20:95-105 (1980)) can be nick-translated and used as a control probe on duplicate filters to confirm the presence or absence of RNA on each blot and to provide a rough standard for use in quantitating differences in α- or β-specific mRNA levels between cell lines. Typical northern and slot blot hybridization and wash conditions are as follows: hybridization in 5×SSPE, 5× Denhardt's solution, 50% formamide, at 42° C. followed by washing in 0.2×SSPE, 0.1% SDS, at 65° C.

B. Nicotine-Binding Assay

Cell lines generated by transfection with chimeric nAChR α- or α- and β-subunit-encoding DNA can be analyzed for their ability to bind nicotine, for example, as compared to control cell lines: neuronally-derived cell lines PC12 (Boulter et al., *Nature* 319(6052):368-74 (1986); ATCC #CRL1721) and IMR32 (Clementi, et al. *Int. J. Neurochem.* 47:291-297 (1986); ATCC #CCL127), and muscle-derived cell line BC3H1 (Patrick, et al., *J. Biol. Chem.* 252:2143-2153 (1977)). Negative control cells (i.e., host cells from which the transfectants are prepared) are also included in the assay. The assay is conducted as follows:

Just prior to being assayed, transfected cells are removed from plates by scraping. Positive control cells used are PC12, BC3H1, and IMR32 (which have been starved for fresh media for seven days). Control cell lines are removed by rinsing in 37° C. assay buffer (50 mM Tris/HCl, 1 mM MgCl$_2$, 2 mM CaCl$_2$, 120 mM NaCl, 3 mM EDTA, 2 mg/ml BSA and 0.1% aprotinin at pH 7.4). The cells are washed and resuspended to a concentration of $1 \times 10^6$/250 μl. To each plastic assay tube is added 250 μl of the cell solution, 15 nM $^3$H-nicotine, with or without 1 mM unlabeled nicotine, and assay buffer to make a final volume of 500 μl. The assays for the transfected cell lines are incubated for 30 min at room temperature; the assays of the positive control cells are incubated for 2 min at 1° C. After the appropriate incubation time, 450 μl aliquots of assay volume are filtered through Whatman GF/C glass fiber filters which has been pretreated by incubation in 0.05% polyethyleneimine for 24 hours at 4° C. The filters are then washed twice, with 4 ml each wash, with ice cold assay buffer. After washing, the filters are dried, added to vials containing 5 ml scintillation fluid and radioactivity is measured.

C. $^{86}$Rb Ion-Flux Assay

The ability of nicotine or nicotine agonists and antagonists to mediate the influx of $^{86}$Rb into transfected and control cells has been found to provide an indication of the presence of functional AChRs on the cell surface. The $^{86}$Rb ion-flux assay is conducted as follows:

1. The night before the experiment, cells are plated at $2 \times 10^6$ per well (i.e., 2 ml per well) in a 6-well polylysine-coated plate.

2. The culture medium is decanted and the plate washed with 2 ml of assay buffer (50 mM HEPES, 260 mM sucrose, 5.4 mM KCl, 1.8 mM CaCl$_2$, 0.8 mM MgSO$_4$, 5.5 mM glucose) at room temperature.

3. The assay buffer is decanted and 1 ml of assay buffer, containing 3 μCi/ml $^{86}$Rb, with 5 mM ouabain and agonist or antagonist in a concentration to effect a maximum response is added.

4. The plate is incubated on ice at 1° C. for 4 min.

5. The buffer is decanted into a waste container and each well was washed with 3 ml of assay buffer, followed by two washes of 2 ml each.

6. The cells are lysed with 2×0.5 ml of 0.2% SDS per well and transferred to a scintillation vial containing 5 ml of scintillation fluid.

7. The radioactivity contained in each vial is measured and the data calculated.

D. Electrophysiological Analysis of Mammalian Cells Transfected with Chimeric nAChR Subunit-Encoding DNA Electrophysiological measurements can be used to assess the activity of recombinant receptors or to assess the ability of a test compound to potentiate, antagonize or otherwise modulate the magnitude and duration of the flow of cations through the ligand-gated recombinant AChR. The function of the expressed neuronal AChR can be assessed by a variety of electrophysiological techniques, including two-electrode voltage clamp and patch clamp methods. The cation-conducting channel intrinsic to the AChR opens in response to acetylcholine (ACh) or other nicotinic cholinergic agonists, permitting the flow of transmembrane current carried predominantly by sodium and potassium ions under physiological conditions. This current can be monitored directly by voltage clamp techniques. In preferred embodiments, transfected mammalian cells or injected oocytes are analyzed electrophysiologically for the presence of AChR agonist-dependent currents.

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

What is claimed is:

1. An isolated polynucleotide encoding a polypeptide comprising the amino acid sequence shown in SEQ ID NO:7, or the complement thereof.

2. A vector comprising the polynucleotide of claim 1.

3. An isolated host cell comprising the vector of claim 2.

4. An isolated polynucleotide comprising the nucleotide sequence shown in SEQ ID NO:6, or the complement thereof.

5. A vector comprising the polynucleotide of claim 4.

6. An isolated host cell comprising the vector of claim 5.

* * * * *